United States Patent
Shechter et al.

(10) Patent No.: US 9,480,751 B2
(45) Date of Patent: Nov. 1, 2016

(54) ALBUMIN BINDING PROBES AND DRUG CONJUGATES THEREOF

(75) Inventors: Yoram Shechter, Rehovot (IL); Matityahu Fridkin, Rehovot (IL)

(73) Assignee: YEDA RESEARCH AND DEVELOPMENT CO. LTD., Rehovot (IL)

(*) Notice: Subject to any disclaimer, the term of this patent is extended or adjusted under 35 U.S.C. 154(b) by 194 days.

(21) Appl. No.: 14/111,347

(22) PCT Filed: Apr. 4, 2012

(86) PCT No.: PCT/IL2012/000149
§ 371 (c)(1),
(2), (4) Date: Oct. 11, 2013

(87) PCT Pub. No.: WO2012/140647
PCT Pub. Date: Oct. 18, 2012

(65) Prior Publication Data
US 2015/0202310 A1    Jul. 23, 2015

Related U.S. Application Data

(60) Provisional application No. 61/473,943, filed on Apr. 11, 2011.

(51) Int. Cl.

| | |
|---|---|
| *A61K 38/00* | (2006.01) |
| *A61K 47/48* | (2006.01) |
| *C07C 309/17* | (2006.01) |
| *C07D 207/46* | (2006.01) |
| *C07D 213/70* | (2006.01) |
| *A61K 38/22* | (2006.01) |
| *A61K 38/28* | (2006.01) |
| *A61K 38/37* | (2006.01) |
| *A61K 38/48* | (2006.01) |

(52) U.S. Cl.
CPC ......... *A61K 47/48038* (2013.01); *A61K 38/22* (2013.01); *A61K 38/28* (2013.01); *A61K 38/37* (2013.01); *A61K 38/4846* (2013.01); *C07C 309/17* (2013.01); *C07D 207/46* (2013.01); *C07D 213/70* (2013.01); *C12Y 304/21021* (2013.01)

(58) Field of Classification Search
None
See application file for complete search history.

(56) References Cited

U.S. PATENT DOCUMENTS

| | | | |
|---|---|---|---|
| 3,070,442 A | 12/1962 | Cohen et al. | |
| 3,080,233 A | 3/1963 | Ruth et al. | |
| 3,112,198 A * | 11/1963 | Klinger | 430/384 |
| 2010/0305032 A1* | 12/2010 | Lau et al. | 514/7.2 |

FOREIGN PATENT DOCUMENTS

| | | |
|---|---|---|
| GB | 893821 | 4/1962 |
| WO | 2010140148 A1 | 9/2010 |

OTHER PUBLICATIONS

Database CA (Online) "11-Sulfoundecanoic acid" (1956).

* cited by examiner

*Primary Examiner* — Jeanette Lieb
(74) *Attorney, Agent, or Firm* — Browdy and Neimark, PLLC

(57) ABSTRACT

The present invention provides a long chain fatty acid (LCFA)-like albumin-binding probe/ligand containing no hydrolysable bond and having an enhanced associating affinity with human serum albumin, which upon conjugation with an amino- or mercapto-containing short-lived drug and administration of the conjugate, significantly prolongs the life time of said drug without substantially interfering with its pharmacological activity. The invention further provides conjugates of said probe with amino- or mercapto-containing drugs, as well as pharmaceutical compositions and uses thereof.

27 Claims, 7 Drawing Sheets

SEQUENCE LISTING

<160> NUMBER OF SEQ ID NOS: 1

<210> SEQ ID NO 1
<211> LENGTH: 41
<212> TYPE: PRT
<213> ORGANISM: Heloderma suspectum

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Asn His
        35                  40

ALBUMIN BINDING PROBES AND DRUG CONJUGATES THEREOF

TECHNICAL FIELD

The present invention relates to albumin-binding probes capable of converting short-lived amino- or mercapto-containing drugs, in particular protein/peptide drugs, into long-lived species in vivo.

Abbreviations: AUC, area under the curve; BSA, bovine serum albumin; DMF, dimethylformamide; EDC, 1-ethyl-3-(3-dimethylaminopropyl) carbodiimide; ESMS, electrospray single quadrupole mass spectroscopy; Ex-4-CO—$(CH_2)_{15}$—$SO_3H$, exendin-4 modified with —$CO(CH_2)_{15}$—$SO_3^-$ moiety; FMS, 2-Sulfo-9-fluorenylmethoxy carbonyl; HPLC, high-performance liquid chromatography; HSA, human serum albumin; $H_3OS$—$(CH_2)_{10}$—COOH, 11-sulfo undecanoic acid; $H_3OS$—$(CH_2)_{15}$—COOH, 16-sulfo hexadecanoic acid; $H_3OS$—$(CH_2)_{10}$—CONHS, 11-sulfo undecanoic-N-hydroxysuccinimide ester; $H_3OS$—$(CH_2)_{15}$—CONHS, 16-sulfo hexadecanoic-N-hydroxysuccinimide ester; Ins-$CO(CH_2)_{15}$—$SO_3H$, insulin modified with —$CO(CH_2)_{15}$—$SO_3^-$ moiety; ITC, isothermal scanning calorimetry; LCFA, long chain fatty acid; NHS, N-hydroxysuccinimide (OSu); PEG, polyethyleneglycol; $PEG_{40}$-NH—CO$(CH_2)_{10}$—$SO_3^-$, 40 kDa PEG chain containing a moiety of —$CO(CH_2)_{10}$—$SO_3^-$; $PEG_{40}$-NH—$CO(CH_2)_{15}$—$SO_3^-$, 40 kDa PEG chain containing a moiety of —$CO(CH_2)_{15}$—$SO_3^-$; $PEG_{40}$-[NH—$CO(CH_2)_{15}$—$SO_3^-]_2$, 40 kDa PEG chain containing two moieties of —$CO(CH_2)_{15}$—$SO_3^-$; TFA, trifluoroacetic acid; TNBS, trinitrobenzene sulfonic acid.

BACKGROUND ART

One of the approaches applied in the last decade for extending the actions of short-lived peptide/protein drugs is to endow them with affinity to serum albumin. This has been achieved by the covalent linking of ligands that bind albumin such as long-chain fatty acids (LCFAs) or bile acids (Kurtzhals et al., 1995; Jonassen et al., 2006; Rolin et al., 2002; Son et al., 2009; Chae et al., 2010). This approach leads to significant elevation in the hydrophobic character of those peptide/protein derivatives and a modest elevation in their affinity towards serum albumin. Bile acids have low association affinity to albumin (Roda et al., 1982) and have considerably lower affinity after linkage to a peptide or a protein. LCFAs such as palmitate associate tightly with albumin, but negligibly if covalently linked via their carboxylate moiety (Peters, 1996; Carter and Ho, 1994). Elevating hydrophobicity of peptide and protein drugs may increase their antigenicity and reduce their bioavailability after subcutaneous administration. Correspondingly, this can alter their pharmacokinetic/pharmacodynamic patterns in an undesirable fashion (Goodman and Gilman, 1995).

Insulin-detemir (Levemir®, NovoNordisk) is a long-acting insulin analog in which LCFA-like probe is integrated into the insulin molecule (Kurtzhals et al., 1995, 1996, 1997). More particular, it is an insulin analog in which the amino acid threonine in position B30 is omitted and myristic acid has been attached to the amino acid lysine in position B29 via the acyl group, i.e., $N^{\epsilon B29}$-tetradecanoyl des(B30) insulin. In the blood, insulin-detemir binds to albumin through the alkyl residue of the myristic acid and it is then slowly dissociated from this complex. Insulin detemir as well as other similar derivatives of insulin are disclosed in U.S. Pat. Nos. 5,750,497, 6,011,007 and 6,869,930, and in US Patent Publication Nos. 20040110664 and 20060030518. These publications disclose an insulin derivative in which (i) the amino acids at positions A21 and B3 are, independently, any amino acid residue which can be coded for by the genetic code except Lys, Arg and Cys; (ii) the amino acid at position B1 is Phe or is deleted; (iii) the amino acid at position B30 is any amino acid residue which can be coded for by the genetic code except Lys, Arg and Cys, or is deleted; and (iv) the amino $\epsilon$-amino group of $Lys^{B29}$ is substituted with an acyl group having at least 10 carbon atoms or a lipophilic substituent having at least 6 carbon atoms, wherein the insulin derivative is a $Zn^{2+}$ complex that is more water soluble than the insulin derivative without $Zn^{2+}$. The technology disclosed in these publications is directed to insulin derivatives only, wherein the lipophilic substituent is linked to the insulin derivative via an amino group on the insulin molecule, preferably the $\epsilon$-amino of the amino acid lysine at position B29, and the insulin derivative is bound to albumin, upon administration, mainly via binding groups present in the albumin molecule capable of binding aliphatic chains.

U.S. Pat. No. 7,186,797 discloses polypeptide conjugates having extended half life in vivo, comprising a polypeptide conjugated to a binding moiety having affinity for albumin. The binding moiety disclosed has two arms, wherein each one of these arms binds to albumin via a certain linking group that is either an aryl moiety or a non-aromatic moiety having 1-10 carbon atoms.

WO 2008/053360 discloses portable albumin binders, capable of binding to albumin through a functional group that is negatively charged or may be deprotonated to yield a negative charge, e.g., a carboxyl group, which are said to be useful for improving the pharmacokinetic properties of diagnostic or therapeutic agents, e.g., by increasing their circulation lifetime.

WO 2005/117984 discloses compounds consisting essentially of a spacer group, a water-soluble bridging group, a fatty acid chain, and an acidic group, preferably carboxyl, phosphonic, phosphinic, sulphinic or sulphonic group, attached to the distal end of said fatty acid chain. As stated in this publication, these compounds are capable of binding to albumin more effectively than such compounds without said acidic group, and are thus used for extending the in vivo serum half-life of proteins or peptides conjugated thereto.

WO 2010/015668 discloses conjugates comprising a protein or glycoprotein such as a blood coagulation factor linked to one or more units each consisting of an albumin binding residue, which is a lipophilic residue negatively charged at physiological pH and capable of non-covalently binding to albumin, linked through a hydrophilic spacer to said protein or glycoprotein. As stated in this publication, the albumin binding residue may be, inter alia, a residue comprising $\omega$-carboxylic acid group or a $\omega$-carboxylic acid isoster such as tetrazol or —$SO_3H$.

US 2010/0305032 discloses compounds comprising polypeptide, e.g., glucagon-like-peptide-1 (GLP-1), derivatives, linked through hydrophilic spacers to albumin binding residues comprising a lipophilic residue; a residue negatively charged at physiological pH; or a residue comprising a group, e.g., —COOH or —$SO_3H$, which can be negatively charged. As stated in this publication, these compounds have protracted profile of action in vivo.

WO 2010/140148 discloses LCFA-like albumin-binding probes containing a spontaneously hydrolysable bond, e.g., HOOC—$(CH_2)_{15}$—S-MAL-FMS-OSu, which efficiently associate with albumin and it is thus capable of converting short-lived amino-containing peptides and proteins to inactive reactivable prodrugs having prolonged lifetime profiles in vivo, without the drawback of inactivation that often occurs upon such derivatization. According to this technology, the drug conjugated with said probe is converted, upon administration and following association with albumin, into a long-lived prodrug, which gradually releases the pharmacologically active constituent under physiological conditions. As stated in this publication, these probes may comprise an acidic group different than —COOH, in particular, —SO$_3$H or —O—PO$_3$H$_2$ group.

SUMMARY OF INVENTION

Contrary to the concept disclosed in WO 2010/140148, according to which a short-lived amino-containing peptide or protein is converted, upon conjugation with a spontaneously hydrolysable bond-containing albumin-binding probe and administration of the conjugate, to an inactive reactivable prodrug that gradually releases the pharmacologically active constituent, the present invention provides LCFA-like albumin-binding probes containing no hydrolysable bond and having an enhanced associating affinity with human serum albumin compared with that of LCFAs, which upon conjugation with either an amino- or mercapto-containing short-lived drug and administration of the conjugate, remarkably prolong the life time of said drug without substantially interfering with its pharmacological activity.

In one aspect, the present invention provides a compound of the general formula I:

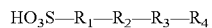

wherein

R$_1$ is selected from (C$_9$-C$_{25}$)alkylene, (C$_9$-C$_{25}$)alkenylene, or (C$_9$-C$_{25}$) alkynylene, optionally substituted by one or more groups each independently selected from halogen, —COR$_5$, —COOR$_5$, —OCOOR$_5$, —OCON(R$_5$)$_2$, —CN, —NO$_2$, —SR$_5$, —OR$_5$, —N(R$_5$)$_2$, —CON(R$_5$)$_2$, —SO$_2$R$_5$, —SO$_3$H, —S(=O)R$_5$, (C$_6$-C$_{10}$)aryl, (C$_1$-C$_4$)alkylene-(C$_6$-C$_{10}$)aryl, heteroaryl, or (C$_1$-C$_4$)alkylene-heteroaryl, and further optionally interrupted by one or more identical or different heteroatoms selected from S, O or N, and/or at least one group each independently selected from —NH—CO—, —CO—NH—, —N(C$_1$-C$_8$alkyl)-, —N(C$_6$-C$_{10}$aryl)-, (C$_6$-C$_{10}$)arylene-diyl, or heteroarylenediyl;

R$_2$ is —CO— or —S—;

R$_3$ is absent or selected from —NH—R$_6$-maleimido, or -maleimido-R$_6$-maleimido;

R$_4$ is absent or a leaving group such as —O—(CH$_2$)$_2$—CN, —Cl, N-hydroxysuccinimide (—OSu), 2-nitrophenoxy, 4-nitrophenoxy, 2,3,4,5,6-pentachloro phenoxy, isoindoline-1,3-dione-2-oxy, benzenesulfanyl, nitrobenzenesulfanyl, pyridine-2-sulfanyl, pyridine-3-sulfanyl, and pyridine-4-sulfanyl;

R$_5$ each independently is H or (C$_1$-C$_8$)alkyl; and

R$_6$ is selected from (C$_1$-C$_{12}$)alkylene, (C$_2$-C$_{12}$)alkenylene, (C$_2$-C$_{12}$)alkynylene, optionally substituted by one or more groups each independently selected from halogen, —COR$_5$, —COOR$_5$, —OCOOR$_5$, —OCON(R$_5$)$_2$, —CN, —NO$_2$, —SR$_5$, —OR$_5$, —N(R$_5$)$_2$, —CON(R$_5$)$_2$, —SO$_2$R$_5$, or —S(=O)R$_5$, and further optionally interrupted by one or more identical or different heteroatoms selected from S, O or N, and/or at least one group each independently selected from —NH—CO—, —CO—NH—, —N(C$_1$-C$_8$alkyl)-, or —N(C$_6$-C$_{10}$aryl)-, provided that (i) when R$_2$ is —CO—, R$_3$ is absent and R$_4$ is a leaving group, or R$_3$ is —NH—R$_6$-maleimido and R$_4$ is absent; and (ii) when R$_2$ is —S—, R$_3$ is absent and R$_4$ is a leaving group, or R$_3$ is -maleimido-R$_6$-maleimido and R$_4$ is absent.

In another aspect, the present invention provides a conjugate of the general formula II:

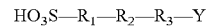

wherein

Y is a moiety of a drug containing at least one amino or mercapto group, linked through said at least one amino or mercapto group;

R$_1$ is selected from (C$_9$-C$_{25}$)alkylene, (C$_9$-C$_{25}$)alkenylene, or (C$_9$-C$_{25}$) alkynylene, optionally substituted by one or more groups each independently selected from halogen, —COR$_5$, —COOR$_5$, —OCOOR$_5$, —OCON(R$_5$)$_2$, —CN, —NO$_2$, —SR$_5$, —OR$_5$, —N(R$_5$)$_2$, —CON(R$_5$)$_2$, —SO$_2$R$_5$, —SO$_3$H, —S(=O)R$_5$, (C$_6$-C$_{10}$)aryl, (C$_1$-C$_4$)alkylene-(C$_6$-C$_{10}$)aryl, heteroaryl, or (C$_1$-C$_4$)alkylene-heteroaryl, and further optionally interrupted by one or more identical or different heteroatoms selected from S, O or N, and/or at least one group each independently selected from —NH—CO—, —CO—NH—, —N(C$_1$-C$_8$alkyl)-, —N(C$_6$-C$_{10}$aryl)-, (C$_6$-C$_{10}$)arylene-diyl, or heteroarylenediyl;

R$_2$ is —CO— or —S—;

R$_3$ is absent or selected from —NH—R$_6$-maleimido, or -maleimido-R$_6$-maleimido;

R$_5$ each independently is H or (C$_1$-C$_8$)alkyl; and

R$_6$ is selected from (C$_1$-C$_{12}$)alkylene, (C$_2$-C$_2$)alkenylene, (C$_2$-C$_{12}$)alkynylene, optionally substituted by one or more groups each independently selected from halogen, —COR$_5$, —COOR$_5$, —OCOOR$_5$, —OCON(R$_5$)$_2$, —CN, —NO$_2$, —SR$_5$, —OR$_5$, —N(R$_5$)$_2$, —CON(R$_5$)$_2$, —SO$_2$R$_5$, or —S(=O)R$_5$, and further optionally interrupted by one or more identical or different heteroatoms selected from S, O or N, and/or at least one group each independently selected from —NH—CO—, —CO—NH—, —N(C$_1$-C$_8$alkyl)-, or —N(C$_6$-C$_{10}$aryl)-, provided that when R$_2$ is —CO— and R$_3$ is absent, Y is linked through said at least one amino group, and when R$_2$ is —S— or R$_3$ is present, Y is linked through said at least one mercapto group.

In a further aspect, the present invention provides a pharmaceutical composition comprising a conjugate of the formula II as defined above, i.e., a conjugate obtained by reacting a compound of formula I with either an amino or mercapto group of the drug Y, or a pharmaceutically acceptable salt thereof, and a pharmaceutically acceptable carrier. The pharmaceutical compositions of the present invention can be used for treatment of various diseases, disorders and conditions in which administration of the drug Y might be useful.

Thus, in another aspect, the present invention relates to a method for treatment of diabetes mellitus or hyperglycemia in an individual in need thereof, said method comprising administering to said individual an effective amount of a conjugate of formula II, as defined above, wherein the drug Y is insulin.

In still another aspect, the present invention relates to a method for treatment of insulin-dependent diabetes mellitus, non-insulin-dependent diabetes mellitus, or gestational diabetes mellitus, or for prevention of hyperglycemia in an individual in need thereof, said method comprising administering to said individual an effective amount of a conjugate a conjugate of formula II, as defined above, wherein the drug Y is exendin-4.

In yet another aspect, the present invention relates to a method for treatment of a patient in need of Factor VIIa or Factor VIII therapy, comprising administering to said patient an effective amount of a conjugate of formula II, as defined above, wherein the drug Y is Factor VIIa or Factor VIII, respectively.

DETAILED DESCRIPTION OF THE INVENTION

Figure 1A:
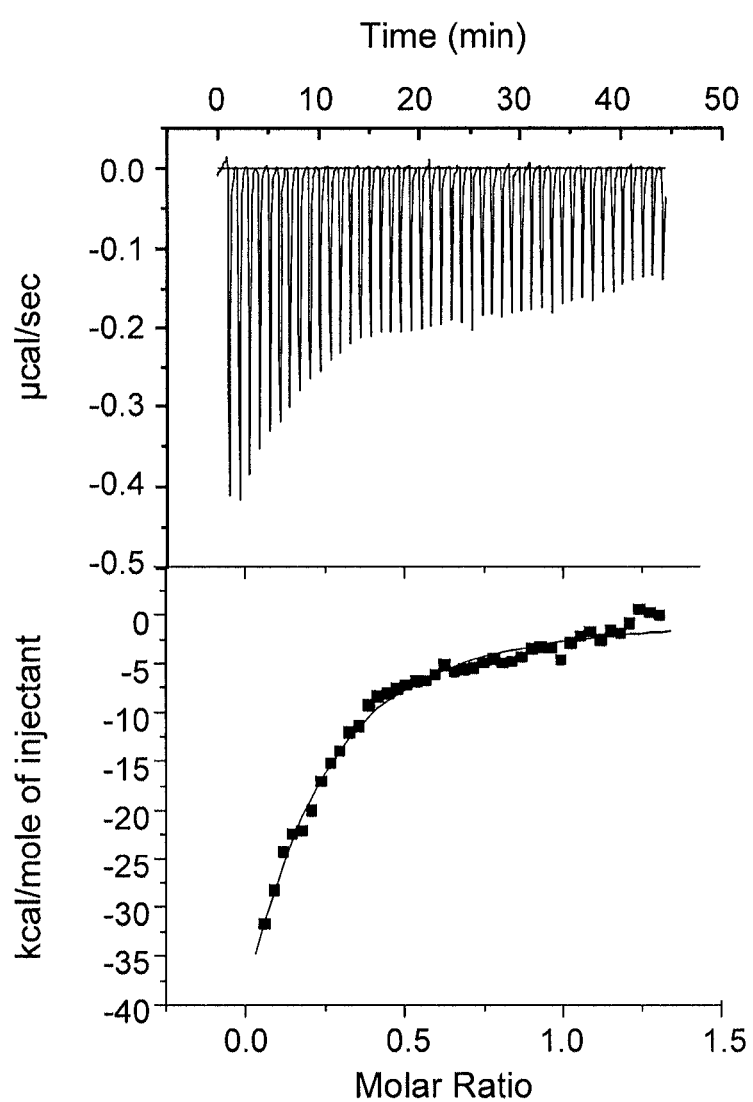
FIGS. 1A-1C show simulating binding isotherms for the association of $PEG_{40}$-NHCO—$(CH_2)_{10}$—$SO_3^-$ (1A), $PEG_{40}$-NHCO—$(CH_2)_{15}$—$SO_3^-$ (1B), and $PEG_{40}$-[NHCO—$(CH_2)_{10}$—$SO_3^-]_2$ (1C) with HSA as determined by ITC-200 (see Experimental hereinafter). 1A—Data: C20HSA400_NDH; Model: OneSites; Chi^2/DoF=9.167E5; N 0.133±0.0351 Sites; K 1.95E5±2.74E4 $M^{-1}$; ΔH −1.075E5±3.127E4 cal/mol; ΔS −337 (cal/mol)/deg. 1B—Data: C20HSA400_NDH; Model: OneSites; Chr^2/DoF=2.106E6; N 0.776±0.0108 Sites; K 8.29E5±8.21E4 $M^{-1}$; ΔH −4.262E4±810.5 cal/mol; ΔS −116 (cal/mol)/deg. 1C—Data: C20HSA400_NDH; Model: OneSites; Chi^2/DoF=6.785E5; N 0.551±0.00565 Sites; K 8.30E5±4.95E4 $M^{-1}$; ΔH −4.800E4±670.3 cal/mol; ΔS −134 (cal/mol)/deg.

Albumin is the most abundant protein in the extracellular fluid. Its concentration is about 0.6 mM in serum and about 0.3 mM in subcutaneous fluid (Poulsen, 1973). Long chain ($C_{16}$-$C_{20}$) fatty acids (LCFAs) are insoluble in body fluids, but turn into a soluble form due to their association with serum albumin and, consequently, transferred and delivered to target tissues. Both the long methylene chain and the C-terminal carboxylate-anion are essential for the high association affinity of LCFA with this carrier protein ($K_a=10^8$-$10^9$ $M^{-1}$; Peters, 1996).

The study described herein was aimed at engineering a new version of reagents containing albumin-binding probes capable of converting short-lived drugs, in particular peptide/protein drugs, into long-lived species in vivo, wherein said probes combining (i) specificity to the α- or ε-amino side-chain moieties, or alternatively, to a mercapto group, if present, thereby permitting linkage to essentially any peptide or protein; (ii) preservation of high affinity to albumin, following covalent attachment to a peptide or protein in a monomodified fashion;

and (iii) minimization of increased hydrophobicity of the resultant derivative. In particular, we investigated whether the carboxylate at the end of a long methylene chain can be replaced with the highly hydrophilic sulfonate anion (—$(CH_2)_n$—$SO_3H$) to generate considerably more hydrophilic peptide/protein derivatives. The sulfonate anion is a highly hydrated anion, surrounded by several molecules of water and having a molecular radius significantly exceeding that of the carboxylate anion, and a key question was whether a methylene-chain ending with a sulfonate anion would maintain the efficacy of LCFA to associate with albumin, and retain sufficient affinity after linkage to a peptide or protein to prolong conjugate stability and residence time significantly in vivo.

11-Mercaptoundecanoic acid and 16-mercaptohexadecanoic acid were converted to the corresponding LCFA-like sulfonated derivatives by performic acid oxidation. The products were obtained in 100% yield in spite of the negligible solubility of the parent molecules in formic acid, and were then turned into active esters by linking N-hydroxysuccinimide (NHS; herein designated —OSu) to the carboxylate moieties using EDC, providing reagents ($HO_3S$—$(CH_2)_{10}$—CONHS and $HO_3S$—$(CH_2)_{15}$—CONHS, respectively) that are capable of selectively reacting with amino moieties of peptides and proteins.

In order to investigate the associating affinity of these reagents, when covalently linked to a drug, toward human serum albumin (HSA), the aforesaid reagents were first linked to a polyethylene glycol molecule of 40 kDa ($PEG_{40}$) comprising an amino group ($PEG_{40}$-$NH_2$) in a monomodified fashion, and the association of the obtained conjugates with HSA was evaluated using isothermal scanning calorimetry (ITC). As shown herein, both $PEG_{40}$-NHCO—$(CH_2)_{10}$—$SO_3^-$ and $PEG_{40}$-NHCO—$(CH_2)_{15}$—$SO_3^-$ associated with HSA, with $K_a$ value of $0.195±0.0274×10^6 M^{-1}$ and $0.829±0.0821×10^6 M^{-1}$, respectively, indicating that HSA has a binding domain for LCFA-like sulfonated molecules as well. Interestingly, $PEG_{40}$ containing a pair of the longer moieties [$PEG_{40}$-(NHCO—$(CH_2)_{15}$—$SO_3^-$)$_2$] associated with HSA with a $K_a$ value of $0.83±0.049×10^6 M^{-1}$, i.e., practically equally to a $PEG_{40}$ containing a sole such moiety, suggesting that unlike the multiple binding domains available for LCFAs (Peters, 1996; Richieri et al., 1993), HSA contains a single binding domain only for sulfonated-LCFA-like molecules.

In view of the fact that the covalent introduction of a single molecule of $HO_3S$—$(CH_2)_{15}$—$CONHS$ to $PEG_{40}$-$NH_2$ yielded a macromolecule that associates with HSA with a $K_a$ exceeding by about 3 times the reported affinity of insulin-detemir to this carrier protein (Markussen et al., 1996), it was envisioned that such associating affinity would be sufficient to significantly extend the actions of short-lived peptides and proteins in vivo. Derivatives of insulin and exendin-4 containing a single such probe were prepared, and as shown herein, subcutaneous administration of insulin-CO—$(CH_2)_{15}$—$SO_3^-$ in mice facilitated a glucose-lowering effect with a $t_{1/2}$ of about 6.4 hours, over 3 fold that obtained with a similar dose of $Zn^{2+}$-free insulin; and subcutaneous and intravenous administration of exendin-4-CO—$(CH_2)_{15}$—$SO_3^-$ into mice yielded prolonged and stable reduction in glucose level with a $t_{1/2}$ value of 28-32 hours, over 5-9 fold longer than that of exendin-4. These findings clearly demonstrate that $HO_3S$—$(CH_2)_{15}$—$CONHS$, a simple and hydrophilic reagent, turns short-lived amino-containing drugs into long-lived species in vivo. Conjugates obtained by nucleophilic substitution of such reagents with amino-containing drugs are thus expected to be neither toxic nor immunogenic.

In one aspect, the present invention thus provides a compound of the general formula I, i.e., an albumin-binding probe/ligand, as defined above.

The term "$(C_1-C_8)$alkyl", as used herein, typically means a straight or branched hydrocarbon radical having 1-8 carbon atoms and includes, e.g., methyl, ethyl, n-propyl, iso-propyl, n-butyl, sec-butyl, isobutyl, tert-butyl, n-pentyl, 2,2-dimethylpropyl, n-hexyl, n-heptyl, n-octyl, and the like.

The term "alkylene" refers to a straight or branched divalent hydrocarbon radical; and the terms "alkenylene" and "alkynylene" typically mean straight or branched divalent hydrocarbon radicals having one or more double or triple bonds, respectively, wherein each one of said double or triple bonds is not a terminal double or triple bond. The terms "$(C_9-C_{25})$alkylene", "$(C_9-C_{25})$alkenylene" and "$(C_9-C_{25})$alkynylene" refer to alkylene, alkenylene and alkynylene, respectively, having 9-25 carbon atoms; the term "$(C_1-C_{12})$alkylene" refers to alkylene having 1-12 carbon atoms; and the terms "$(C_2-C_{12})$alkenylene" and "$(C_2-C_{12})$alkynylene" refer to alkenylene and alkynylene, respectively, having 2-12 carbon atoms.

Examples of alkylenes include, without being limited to, methylene, ethylene, propylene, butylene, 2-methylpropylene, pentylene, 2-methylbutylene, hexylene, 2-methylpentylene, 3-methylpentylene, 2,3-dimethylbutylene, heptylene, octylene, n-tridecanylene, n-tetradecanylene, n-pentadecanylene, n-hexadecanylene, n-heptadecanylene, n-octadecanylene, n-nonadecanylene, icosanylene, henicosanylene, docosanylene, tricosanylene, tetracosanylene, pentacosanylene, and the like. Non-limiting examples of alkenylenes and alkynylenes include 2-, 3-, 4-, 5- and 6-tridecenylene, tetradecenylenes such as myristoleylene, 2-, 3-, 4-, 5-, 6- and 7-pentadecenylene, hexadecenylenes such as palmitoleylene, 2-, 3-, 4-, 5-, 6-, 7- and 8-heptadecenylene, octadecenylenes such as oleylene, linoleylene, α-linoleylene, nonadecenylene, icosenylenes such as arachidonylene and eicosapentylene, henicosenylene, docosenylene, tricosenylene, tetracosenylene, pentacosenylene, and the like.

The term "$(C_6-C_{10})$aryl" denotes an aromatic carbocyclic group having 6-10 carbon atoms consisting of a single ring or condensed multiple rings such as, but not limited to, phenyl and naphthyl. The aryl may optionally be substituted by one or more, groups each independently selected from halogen, —OH, —COOH, —CN, —$NO_2$, —SH, or —$CONH_2$. The term "$(C_6-C_{10})$arylene-diyl" refers to a divalent radical derived from a "$(C_6-C_{10})$aryl" as defined herein by removal of two hydrogen atoms from any of the ring atoms.

The term "heteroaryl" refers to a radical derived from a 5-10-membered mono- or poly-cyclic heteroaromatic ring containing one to three, preferably 1-2, heteroatoms selected from N, O, or S. Examples of mono-cyclic heteroaryls include, without being limited to, pyrrolyl, furyl, thienyl, thiazinyl, pyrazolyl, pyrazinyl, imidazolyl, oxazolyl, isoxazolyl, thiazolyl, isothiazolyl, pyridyl, pyrimidinyl, 1,2,3-triazinyl, 1,3,4-triazinyl, and 1,3,5-triazinyl. Polycyclic heteroaryl radicals are preferably composed of two rings such as, but not limited to, benzofuryl, isobenzofuryl, benzothienyl, indolyl, quinolinyl, isoquinolinyl, imidazo[1,2-a]pyridyl, benzimidazolyl, benzthiazolyl, benzoxazolyl, pyrido[1,2-a]pyrimidinyl and 1,3-benzodioxinyl. The heteroaryl may optionally be substituted by one or more groups each independently selected from halogen, —OH, —COOH, —CN, —$NO_2$, —SH, or —$CONH_2$. It is to be understood that when a polycyclic heteroaryl is substituted, the substitution may be in any of the carbocyclic and/or heterocyclic rings. The term "heteroarylenediyl" denotes a divalent radical derived from a "heteroatyl" as defined herein by removal of two hydrogen atoms from any of the ring atoms.

The term "halogen" as used herein refers to a halogen and includes fluoro, chloro, bromo, and iodo, and it is preferably fluoro or chloro.

The term "leaving group", as used herein, refers to any functional group or atom, which can be displaced by another functional group or atom in a substitution reaction, e.g., a nucleophilic substitution reaction. Non-limiting examples of leaving groups include —O—$(CH)_2$—CN, —Cl, 2,5-dioxopyrrolidin-1-olate also known as N-hydroxysuccinimide (—OSu), 2-nitrophenoxy, 4-nitrophenoxy, 2,3,4,5,6-pentachloro phenoxy, isoindoline-1,3-dione-2-oxy, benzenesulfanyl, nitrobenzenesulfanyl, pyridine-2-sulfanyl, pyridine-3-sulfanyl, and pyridine-4-sulfanyl, preferably —OSu. The chemical structures of these leaving groups are shown in Table 1 hereinafter.

TABLE 1

Examples of leaving groups represented by $R_4$ in the general formula I

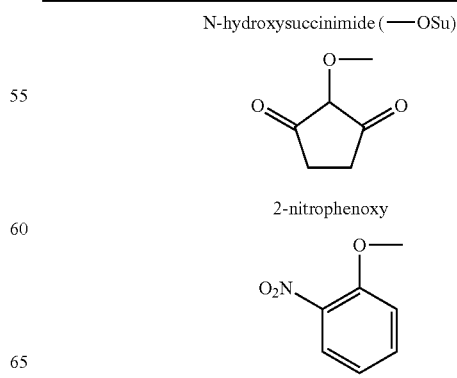

TABLE 1-continued

Examples of leaving groups represented by $R_4$ in the general formula I 4-nitrophenoxy

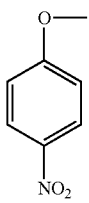

2,3,4,5,6-pentachlorophenoxy

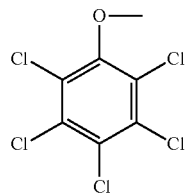

isoindoline-1,3-dione-2-oxy

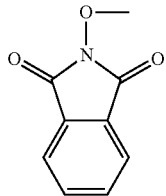

benzenesulfanyl

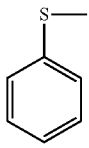

nitrobenzenesulfanyl

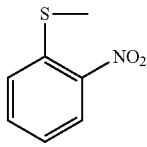

pyridine-2-sulfanyl

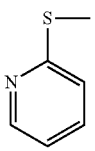

pyridine-3-sulfanyl

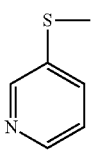

TABLE 1-continued

Examples of leaving groups represented by $R_4$ in the general formula I pyridine-4-sulfanyl

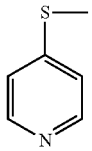

In certain embodiments, the compound of the present invention is a compound of the general formula I, wherein $R_1$ is $(C_9-C_{25})$alkylene, preferably $(C_{10}-C_{20})$alkylene, more preferably $(C_{14}-C_{18})$alkylene, optionally substituted by one or more groups each independently selected from halogen, —$COR_5$, —$COOR_5$, —$OCOOR_5$, —$OCON(R_5)_2$, —CN, —$NO_2$, —$SR_5$, —$OR_5$, —$N(R_5)_2$, —$CON(R_5)_2$, —$SO_2R_5$, —$SO_3H$, —$S(=O)R_5$, $(C_1-C_2)$alkylene-$(C_6-C_{10})$aryl, or $(C_1-C_2)$alkylene-heteroaryl, wherein $R_5$ is H, and further optionally interrupted by one or more identical or different heteroatoms selected from S, O or N, and/or at least one group each independently is —NH—CO—, or —CO—NH—. In particular such embodiments, the $(C_6-C_{10})$aryl is phenyl, hydroxyphenyl, carboxyphenyl, nitrophenyl, cyanophenyl, mercaptophenyl, aminocarbonylphenyl, fluorophenyl, chlorophenyl, or bromophenyl; and the heteroaryl is 2-indolyl, 3-indolyl, 4-indolyl, 5-indolyl, 6-indolyl, 7-indolyl, 2-imidazolyl, 4-imidazolyl, or 5-imidazolyl, preferably phenyl, hydroxyphenyl, 2-indolyl, or 4-imidazolyl. Preferred compounds are those wherein $R_1$ is either $(C_{10}-C_{20})$alkylene, preferably $(C_{14}-C_{18})$alkylene; or $(C_{10}-C_{20})$alkylene, preferably $(C_{14}-C_{18})$alkylene, substituted by one or more groups each independently is —$CH_2$—$(C_6-C_{10})$aryl, and further interrupted by at least one group each independently is —NH—CO—, or —CO—NH—. More preferred compounds are those wherein $R_1$ is —$(CH_2)_{10}$—, —$(CH_2)_{15}$—, —$(CH_2)_{10}$—CO—NH—CH($CH_2$-phenyl)-, or —$(CH_2)_{15}$—CO—NH—CH($CH_2$-phenyl)-.

The albumin-binding probes of the invention have an enhanced associating affinity with human serum albumin compared with that of LCFAs. Moreover, some of these ligands, in particular those in which $R_1$ in the general formula I is substituted by one or more aryl- or heteroaryl-containing groups, i.e., by one or more groups selected from $(C_1-C_2)$alkylene-$(C_6-C_{10})$aryl or $(C_1-C_2)$alkylene-heteroaryl, may be capable of further associating with HSA via said one or more aryl or heteroaryl moieties. Consequently, such compounds may associate with HSA with a $K_a$ value that is even higher than that of the compounds comprising sulfonate anion only.

Certain albumin-binding probes of the invention, and particularly those of the formula $HO_3S$—$(CH_2)_{10}$—CO—OSu or $HO_3S$—$(CH_2)_{15}$—CO—OSu exemplified herein, are capable of selectively reacting with any amino-containing drugs, particularly peptide and protein drugs, by nucleophilic substitution of the leaving group with an amino group of the drug, e.g., the α-amino group or an ε-amino group such as of a lysine residue, if present, in cases wherein said drug is a peptide or protein. Nevertheless, although peptide and protein drugs can undergo a considerable degree of lysine modification before being substantially inactivated, in case more than one amino group is present in the drug, the amino group to be linked to said albumin-binding probe should be selected such as to minimally interfere with the pharmacological activity of the drug.

In cases wherein conjugation with an albumin-binding probe of the invention without substantially interfering with the pharmacological activity of the drug cannot be performed through the amino group(s) present; but a non-bonded cysteine residue, i.e., a cysteine residue having a free mercapto group, is present and can be modified without substantially interfering with the pharmacological activity of the drug, albumin-binding probes of the invention capable of selectively reacting with a mercapto group can be used. In such cases, either nucleophilic addition of the mercapto-containing drug to an alpha, beta unsaturated carbonyl moiety (e.g., of maleimido) of the albumin-binding probe, or a thiol-disulfide exchange reaction between a mercapto group of the mercapto-containing drug and a thiol residue of said albumin binding probe, is performed.

It cases neither amino nor mercapto group suitable for modification without interfering with the pharmacological activity of the drug is present, an amino acid of the drug at a position suitable for modification can be replaced with an ε-amino group-containing amino acid such as lysine, so as to provide an additional side-chain amino group through which an albumin-binding probe capable of selectively reacting with an amino group can then be linked to form a conjugate. Alternatively, an amino acid of the drug can be replaced by a non-bonded cysteine, or a non-bonded cysteine residue can be added to the drug at any position, to thereby provide a mercapto group through which an albumin binding probe capable of selectively reacting with a mercapto group can then be linked to form a conjugate.

The replacement of an amino acid of the peptide or protein drug with either an ε-amino group-containing amino acid or a non-bonded cysteine, and the addition of a non-bonded cysteine residue to the drug, can be performed using any technology known in the art, e.g., during solid-phase synthesis of said protein or peptide in which a non-bonded cysteine is added, or by recombinant technology in which one of the amino acids in the polypeptide-chain is replaced by an ε-amino group-containing amino acid such as lysine or cysteine. In any case, a modification to provide either an ε-amino group-containing amino acid or non-bonded cysteine residue as described above should be performed such as to minimally interfere with the pharmacological activity of said drug.

In certain embodiments, the compound of the present invention is a compound of the general formula I with $R_1$ as defined above, wherein $R_2$ is —CO—, i.e., a compound of the general formula $HO_3S$—$R_1$—CO—$R_3$—$R_4$, herein identified Ia.

In certain particular embodiments, the compound of the invention is a compound of the general formula Ia, capable of reacting with an amino-containing drug, wherein $R_3$ is absent, and $R_4$ is a leaving group such as —O—$(CH)_2$—CN, N-hydroxysuccinimide (—OSu), 2-nitrophenoxy, 4-nitrophenoxy, 2,3,4,5,6-pentachloro phenoxy, isoindoline-1,3-dione-2-oxy, benzenesulfanyl, nitrobenzenesulfanyl, pyridine-2-sulfanyl, pyridine-3-sulfanyl, or pyridine-4-sulfanyl, preferably —Osu, i.e., a compound of the general formula $HO_3S$—$R_1$—CO-leaving group, herein identified Ia-1.

In other particular embodiments, the compound of the invention is a compound of the general formula Ia, capable of reacting with a mercapto-containing drug, wherein $R_3$ is —NH—$R_6$-maleimido, and $R_4$ is absent, i.e., a compound of the general formula $HO_3S$—$R_1$—CO—NH—$R_6$-maleimido, herein identified Ia-2. In more particular such embodiments, $R_6$ is $(C_1-C_{12})$alkylene, preferably $(C_1-C_{10})$alkylene, more preferably $(C_1-C_8)$alkylene, optionally substituted by one or more groups each independently selected from halogen, —$COR_5$, —$COOR_5$, —$OCOOR_5$, —$OCON(R_5)_2$, —CN, —$NO_2$, —$SR_5$, —$OR_5$, —$N(R_5)_2$, —$CON(R_5)_2$, —$SO_2(R_5)$, or —S(=O)$R_5$, wherein $R_5$ is H, and further optionally interrupted by one or more identical or different heteroatoms selected from S, O or N, and/or at least one group each independently is —NH—CO—, or —CO—NH—. In preferred embodiments, $R_6$ is either $(C_1-C_{10})$alkylene, preferably $(C_1-C_8)$alkylene; or $(C_1-C_{10})$alkylene, preferably $(C_1-C_8)$alkylene, interrupted by one or more groups each independently is —NH—CO—, or —CO—NH—. In more preferred embodiments, $R_6$ is —$CH_2$—, —$(CH_2)_3$—, —$(CH_2)_3$—NH—CO—$(CH_2)_3$—, or —$(CH_2)_2$—NH—CO—$(CH_2)_5$—.

In certain embodiments, the compound of the present invention is a compound of the general formula I with $R_1$ as defined above, wherein $R_2$ is —S—, i.e., a compound of the general formula $HO_3S$—$R_1$—S—$R_3$—$R_4$, herein identified Ib, capable of reacting with a mercapto-containing drug.

In certain particular embodiments, the compound of the invention is a compound of the general formula Ib, wherein $R_3$ is absent, and $R_4$ is a leaving group selected from benzenesulfanyl, nitrobenzenesulfanyl, pyridine-2-sulfanyl, pyridine-3-sulfanyl, or pyridine-4-sulfanyl, preferably pyridine-2-sulfanyl, or pyridine-4-sulfanyl, i.e., a compound of the general formula $HO_3S$—$R_1$—S-leaving group, herein identified Ib-1.

In other particular embodiments, the compound of the invention is a compound of the general formula Ib, wherein $R_3$ is -maleimido-$R_6$-maleimido, and $R_4$ is absent, i.e., a compound of the general formula $HO_3S$—$R_1$—S-maleimido-$R_6$-maleimido, herein identified Ib-2. In more particular such embodiments, $R_6$ is $(C_1-C_{12})$alkylene, preferably $(C_1-C_{10})$alkylene, more preferably $(C_1-C_8)$alkylene, optionally substituted by one or more groups each independently selected from halogen, —$COR_5$, —$COOR_5$, —$OCOOR_5$, —$OCON(R_5)_2$, —CN, —$NO_2$, —$SR_5$, —$OR_5$, —$N(R_5)_2$, —$CON(R_5)_2$, —$SO_2(R_5)$, or —S(=O)$R_5$, wherein $R_5$ is H, and further optionally interrupted by one or more identical or different heteroatoms selected from S, O or N, and/or at least one group each independently is —NH—CO—, or —CO—NH—. In preferred embodiments, $R_6$ is either $(C_1-C_{10})$alkylene, preferably $(C_1-C_8)$alkylene, more preferably $(C_1-C_6)$alkylene; or $(C_1-C_{10})$alkylene, preferably $(C_1-C_8)$alkylene, more preferably $(C_1-C_6)$alkylene, interrupted by one or more groups each independently is —NH—CO—, or —CO—NH—.

The specific compounds of the general formula I described in the specification are herein identified by the Arabic numbers 1-14 in bold, and their specific formulas are depicted in Table 2 hereinafter.

In certain specific embodiments, the compound of the invention is a compound of the general formula Ia-1, more particularly, a compound of the general formula I, wherein $R_1$ is —$(CH_2)_{10}$—, —$(CH_2)_{15}$—, —$(CH_2)_{10}$—CO—NH—CH($CH_2$-phenyl)-, or —$(CH_2)_{15}$—CO—NH—CH($CH_2$-phenyl)-; $R_2$ is —CO—; $R_3$ is absent; and $R_4$ is —Osu, i.e., the compound $HO_3S$—$(CH_2)_{10}$—CO—OSu, $HO_3S$—$(CH_2)_{15}$—CO—OSu, $HO_3S$—$(CH_2)_{10}$—CO—NH—CH($CH_2$-phenyl)-CO—OSu, or $HO_3S$—$(CH_2)_{15}$—CO—NH—CH($CH_2$-phenyl)-CO—OSu (herein identified compounds 1, 2, 3 and 4, respectively).

In other specific embodiments, the compound of the invention is a compound of the general formula Ia-2, more particularly, a compound of the general formula I, wherein $R_1$ is —$(CH_2)_{10}$—, or —$(CH_2)_{15}$—; $R_2$ is —CO—; $R_3$ is —NH—$R_6$-maleimido; $R_4$ is absent; and $R_6$ is —$CH_2$—, —$(CH_2)_2$—, —$(CH_2)_3$—NH—CO—$(CH_2)_3$—, or —$(CH_2)_2$—NH—CO—$(CH_2)_5$—, i.e., the compound $HO_3S$—$(CH_2)_{10}$—CO—NH—$CH_2$-maleomido, $HO_3S$—$(CH_2)_{10}$—CO—NH—$(CH_2)_3$-maleimido, $HO_3S$—$(CH_2)_{10}$—CO—NH—$(CH_2)_3$—NH—CO—$(CH_2)_3$-maleimido, $HO_3S$—$(CH_2)_{10}$—CO—NH—$(CH_2)_2$—NH—CO—$(CH_2)_5$- maleimido, $HO_3S$—$(CH_2)_{15}$—CO—NH—$CH_2$-maleimido, $HO_3S$—$(CH_2)_{15}$—CO—NH—$(CH_2)_3$-maleimido, $HO_3S$—$(CH_2)_{15}$—CO—NH—$(CH_2)_3$—NH—CO—$(CH_2)_3$-maleimido, or $HO_3S$—$(CH_2)_{15}$—CO—NH—$(CH_2)_2$—NH—CO—$(CH_2)_5$-maleimido (herein identified compounds 5, 6, 7, 8, 9, 10, 11 and 12, respectively).

In further specific embodiments, the compound of the invention is a compound of the general formula Ib-1, more particularly, a compound of the general formula I, wherein $R_1$ is —$(CH_2)_{15}$—; $R_2$ is —S—; $R_3$ is absent; and $R_4$ is pyridine-2-sulfanyl, or pyridine-4-sulfanyl, i.e., the compound $HO_3S$—$(CH_2)_{15}$—S-pyridine-2-sulfanyl, or $HO_3S$—$(CH_2)_{15}$—S-pyridine-4-sulfanyl (herein identified compounds 13 and 14, respectively).

TABLE 2

Specific compounds of the general formula I described herein

| Compound | General formula | Specific formula |
|---|---|---|
| 1 | Ia-1 | $HO_3S$—$(CH_2)_{10}$—CO—OSu |
| 2 | Ia-1 | $HO_3S$—$(CH_2)_{15}$—CO—OSu |
| 3 | Ia-1 | $HO_3S$—$(CH_2)_{10}$—CO—NH—CH($CH_2$-phenyl)—CO—OSu |
| 4 | Ia-1 | $HO_3S$—$(CH_2)_{15}$—CO—NH—CH($CH_2$-phenyl)—CO—OSu |
| 5 | Ia-2 | $HO_3S$—$(CH_2)_{10}$—CO—NH—$CH_2$-aleimido |
| 6 | Ia-2 | $HO_3S$—$(CH_2)_{10}$—CO—NH—$(CH_2)_3$-aleimido |
| 7 | Ia-2 | $HO_3S$—$(CH_2)_{10}$—CO—NH—$(CH_2)_3$—NH—CO—$(CH_2)_3$-maleimido |
| 8 | Ia-2 | $HO_3S$—$(CH_2)_{10}$—CO—NH—$(CH_2)_2$—NH—CO—$(CH_2)_5$-maleimido |
| 9 | Ia-2 | $HO_3S$—$(CH_2)_{15}$—CO—NH—$CH_2$-maleimido |
| 10 | Ia-2 | $HO_3S$—$(CH_2)_{15}$—CO—NH—$(CH_2)_3$-maleimido |
| 11 | Ia-2 | $HO_3S$—$(CH_2)_{15}$—CO—NH—$(CH_2)_3$—NH—CO—$(CH_2)_3$-maleimido |
| 12 | Ia-2 | $HO_3S$—$(CH_2)_{15}$—CO—NH—$(CH_2)_2$—NH—CO—$(CH_2)_5$-maleimido |
| 13 | Ib-1 | $HO_3S$—$(CH_2)_{15}$—S-pyridine-2-sulfanyl |
| 14 | Ib-1 | $HO_3S$—$(CH_2)_{15}$—S-pyridine-4-sulfanyl |

The compounds of the present invention may be prepared according to any technology or procedure known in the art, e.g., as described with respect to compounds 1, 2, 6 and 10 in the Examples section hereinafter; and their binding properties to HSA can be evaluated by any suitable technique, e.g., by ITC as exemplified herein.

In another aspect, the present invention relates to a conjugate of the formula II as defined above. This conjugate may be obtained by reacting a compound of the formula I as defined above with an amino- or mercapto-containing drug, more particularly, by (i) nucleophilic substitution of the leaving group $R_4$ in a compound having the general formula Ia-1 with an amino group of said amino-containing drug; (ii) Michael addition, i.e., nucleoohilic addition of a mercapto-containing drug to the C=C bond of the maleimido moiety in a compound having the general formula 1a-2 or Ib-2; or (iii) thiol-disulfide exchange reaction in which a new disulfide bond is formed between $R_2$ in a compound of the general formula Ib-1 and a mercapto group of a mercapto-containing drug while the leaving group $R_4$ is released.

The drug according to the present invention may be any drug containing at least one amino or mercapto, i.e., thio, group. Nevertheless, whereas proteins and peptides in general can undergo a considerable degree of lysine modifications before being substantially inactivated, this may not be the case for low molecular weight drugs such as amino acid derivatives, catecholamines and aminoglycosides, which may suffer a massive loss of pharmacological potency upon conjugation. The technology disclosed herein, according to which the life time of an amino- or mercapto-group containing short-lived drug is prolonged by introduction of an LCFA-like albumin-binding probe containing no hydrolysable bond, is thus restricted to such drugs, e.g., proteins and peptides (including polypeptides) as well as certain small molecules, which do not significantly lose their biological/pharmacological activity upon introduction of said probe to the drug molecule. In cases of low molecular weight drugs such as amino acid derivatives, catecholamines and aminoglycosides, the strategy of introducing a slowly hydrolyzable albumin-binding probe, previously disclosed (Sasson et al., 2010; WO 2010/140148), is recommended.

In certain embodiments, the drug according to the invention is a peptide or a protein drug of low or medium molecular weight such as, without being limited to, insulin, an interferon, preferably IFN-α2, a peptide YY (PYY) agonist, preferably the peptide $PYY_{3-36}$, an exendin, preferably exendin-3 or exendin-4, an exendin analog or exendin agonist, atrial natriuretic peptide (ANP), human growth hormone (hGH), erythropoietin, TNF-α, calcitonin, gonadotropin releasing hormone (GnRH), a GnRH analog, hirudin, glucagon, a coagulation factor such as Factor VIIa and Factor VIII, and a monoclonal antibody fragment, preferably anti-TNF-α monoclonal antibody fragment. In should be understood that any of the peptide or protein drugs used according to the invention may be either natural or recombinant.

As stated above, in cases said peptide or protein comprises a non-bonded cysteine residue containing a free mercapto group, said peptide or protein can be linked to an albumin-binding probe of the general formula Ia-1 via one of the amino groups thereof or, alternatively, to an albumin-binding probe of the general formula Ia-2, Ib-1 or Ib-2 via a free mercapto group thereof. As stated above, the conjugation of said peptide or protein drug to an albumin-binding probe of the invention should be performed so as to minimally interfere with the pharmacological activity of the drug; and modification of the drug so as to provide an additional amino group or a mercapto group can be performed as described above, if necessary.

In certain cases, the modification of the low or medium molecular weight protein or peptide with an albumin-binding probe of the general formula Ia-1 can be simply applied as the last step of a solid-phase peptide synthesis, selectively linking said probe to the α-amino side-chain, prior to deprotection of the lysine moieties. This approach can turn any peptide that can therapeutically tolerate an additional molecule at its N-terminal position into an albumin binding species, with prolonged residence time in vivo, as well as resistance to degradation by serum amino peptidases.

In certain other embodiments, the drug according to the invention is a small molecule, which does not suffer a massive loss of pharmacological potency upon conjugation to an albumin-binding probe of the invention. Examples of such drugs include, without being limited to, aminoglycosides and antibacterial molecules related thereto, anticancer drugs such as aminopterin, and antiviral drugs such as acyclovir.

Insulin is the predominant drug for diabetes mellitus, a group of syndromes characterized by hyperglycemia, altered metabolism of lipids, carbohydrates and proteins, and an increased risk of complications from vascular diseases. Most patients can clinically be classified as having either insulin-dependent (Type I) or insulin-independent diabetes mellitus (Type II). About 90% of diabetic patients in the Western world have Type II diabetes, and about 70% of the Type II diabetics in the United States are also obese, a factor that significantly contributes to insulin resistance. Whereas in Type I diabetes, there is an extensive and selective loss of pancreatic β-cells and a state of hypoinsulinemia, there is no significant loss of β-cells from the islets in Type II diabetic patients, in which patients the mean plasma concentration of insulin over a 24-hour period is essentially normal or even elevated because of peripheral resistance to the action of the hormone. Nevertheless, individuals with Type II diabetes are relatively insulin deficient, as a normal pancreatic β-cell should be capable of secreting amounts of insulin that are considerably greater than normal when confronted with hyperglycemia, thus allowing an individual to maintain euglycemia in the face of moderate resistance to insulin.

Virtually all forms of diabetes mellitus are due to either a decrease in the circulating concentration of insulin (insulin deficiency) or a decrease in response of peripheral tissues to insulin (insulin resistance), in association with an excess of hormones with actions opposite to those of insulin, i.e., glucagon, growth hormone, cortisol and catecholamines.

The $t_{1/2}$ of insulin in plasma is about 5-6 min, wherein the degradation of insulin occurs primarily in liver and to a lesser extent in kidney and muscle. Proteolytic degradation of insulin in the liver is primarily receptor mediated. Various modifications have been described in order to create insulin analogs having longer half-lives in the blood circulation, in particular, prodrugs capable of releasing active insulin into the circulation over a relatively long time period, i.e., 8-24 hours, intended to provide the required basal level of insulin for a whole day. One of such long-acting human insulin analogs is the aforesaid insulin detemir (Levemir®, NovoNordisk), produced by a process including expression of recombinant DNA in *Saccharomyces cerevisiae* followed by chemical modification, which said to have up to 24 hours duration of action. In particular, insulin detemir is an insulin analog in which the amino acid threonine in position B30 is omitted and myristic acid has been attached to the amino acid lysine in position B29, i.e., $N^{\epsilon B29}$-tetradecanoyl des (B30) insulin. In the blood, insulin-detemir binds to albumin through the acyl group at position B29 and it is then slowly dissociated from this complex.

As shown in Example 4 hereinafter, a conjugate according to the present invention formed by introducing insulin to a compound of the general formula Ia-1, in particular, the conjugate $HO_3S-(CH_2)_{15}-CO$-insulin formed by introducing insulin to compound 2, had a flat glucose-lowering pattern ($t_{1/2}$=6.4±0.3 hours), which was about 3-fold more prolonged than that of insulin ($t_{1/2}$=2±0.2 hours), and about 20% the biological potency of insulin.

Thus, in certain embodiments, the conjugate of the present invention is obtained by nucleophilic substitution of a compound of the general formula Ia-1, preferably, compound 1, 2, 3 or 4, with any of the amino groups of insulin.

Exendins are peptides found in the venom of the Gila-monster, a lizard found in Arizona, and the Mexican Beaded Lizard. Exendin-3 is present in the venom of *Heloderma horridum*, and exendin-4 is present in the venom of *Heloderma suspectum*. The exendins have some sequence similarity to several members of the glucagon-like peptide family, with the highest homology, 53%, being to GLP-1[7-36]NH$_2$, which is also known as proglucagon, and has an insulinotropic effect, stimulating insulin secretion from pancreatic β-cells. Exendin-4 is composed of 39 amino acid residues with the carboxy terminus amidated. Exendin-4 potently binds at GLP-1 receptors on insulin-secreting βTC1 cells, at dispersed acinar cells from guinea pig pancreas, and at parietal cells from stomach. The use of exendin-3 and exendin-4 as insulinotrophic agents for the treatment of diabetes mellitus and the prevention of hyperglycemia has been previously proposed, e.g., in U.S. Pat. No. 5,424,286.

The glucose-lowering profile of native exendin-4 was compared with that of an exendin-4-based conjugate according to the present invention, in particular, the conjugate $HO_3S-(CH_2)_{15}-CO$-exendin-4 formed by introducing exendin-4 to compound 2, and as shown in Example 5, following subcutaneous administration of the conjugate to CD1 mice, glucose level fall to 70+5 mg/dl, and remained at low level over a period of ~24 hours before slowly returning to the level of the saline-injected mice. A $t_{1/2}$ value of 32±2 hours, which is 5.5 times longer than that obtained by the same dose of the native hormone, was obtained; and the area under the curve of subcutaneously administered conjugate exceeded 7±0.1 times that obtained by a similar subcutaneously administered dose of the native hormone. Intravenously administered conjugate yielded a prolonged glucose-lowering pattern having a $t_{1/2}$ value of 28±2 hours exceeding that of exendin-4 by 9-10 folds (blood glucose level was still low 48 hours after administration, which was the last time point measured), indicating that the prolonged-acting feature of the conjugate appears to be predominantly the outcome of its association with circulating serum albumin.

Thus, in other certain embodiments, the conjugate of the present invention is obtained by nucleophilic substitution of a compound of the general formula Ia-1, preferably, compound 1, 2, 3 or 4, with any of the amino groups of exendin-4.

Factor VII (FVII), formerly known as proconvertin, is a vitamin K dependent enzyme of the serine protease class, produced in the liver, and is one of the central proteins in the coagulation cascade. The main role of FVII is to initiate the process of coagulation in conjunction with tissue factor, which is found on the outside of blood vessels, normally not exposed to the bloodstream. Upon vessel injury, tissue factor is exposed to the blood and circulating FVII. Once bound to tissue factor, FVII is converted to activated FVII (FVIIa) by different proteases, among which are thrombin (Factor IIa), activated Factor X and the FVIIa-tissue factor complex itself. The most important substrates for FVIIa-tissue factor are Factors X (FX) and IX (FIX).

Recombinant human FVIIa has been introduced for use in uncontrollable bleeding in hemophilia patients with Factor VIII (FVIII) or FIX deficiency, who have developed inhibitors against replacement coagulation factor. This factor is increasingly used in uncontrollable hemorrhage, as it induces coagulation only in those sites where tissue factor is present as well. In addition, according to Mayer et al. (2005), recombinant human FVII improves outcomes in acute intracerebral hemorrhage.

FVIII is another essential blood clotting factor. In fact, it is a cofactor for activated FIX which, in the presence of $Ca^{+2}$ and phospholipids, forms a complex that converts FX to the activated form thereof. In human, FVIII is encoded by the F8 gene, and therefore defects in this gene result in hemophilia A, a common recessive X-linked coagulation disorder. The FVIII gene produces two alternatively spliced transcripts, wherein transcript variant 1 encodes a large glycoprotein, isoform a, which circulates in plasma, associates with von Willebrand factor in a noncovalent complex and undergoes multiple cleavage events, and transcript variant 2 encodes a putative small protein, isoform b, which consists primarily of the phospholipid binding domain of FVIIIc that is essential for coagulant activity.

U.S. Pat. No. 7,199,223 discloses conjugates of a FVIII moiety and one or more water-soluble polymers, each having a molecular weight in the range of 6 to 150 kDa, preferably conjugates wherein each one of the polymers is a poly(alkylene oxide), more preferably a PEG, and the FVIII moiety is either recombinantly produced or blood-derived FVIII, FVIIIa, FVIII:C, FVIII:vWF, and B-domain deleted FVIII. As described in this patent, these conjugates may be used for treating patients in need of FVIII therapy such as patients suffering from hemophilia A. US Publication Nos. 20080058504 and 20090041714, both continuation applications of U.S. Pat. No. 7,199,223, discloses similar conjugates, wherein a water-soluble polymer is covalently attached to the FVIII moiety via either a degradable linkage such as a physiologically hydrolyzable or enzymatically degradable linkage, or a thiol group of a cysteine residue contained within said FVIII moiety.

In further certain embodiments, the conjugate of the present invention is obtained by nucleophilic substitution of a compound of the general formula Ia-1, preferably compound 1, 2, 3 or 4, with any of the amino groups of FVIIa or FVIII.

In a further aspect, the present invention provides a pharmaceutical composition comprising a conjugate of the formula II as defined above, or a pharmaceutically acceptable salt thereof, and a pharmaceutically acceptable carrier.

In certain embodiments, the pharmaceutical composition of the present invention comprises a conjugate obtained by nucleophilic substitution of a compound of the general formula Ia-1, preferably compound 1, 2, 3 or 4, with insulin, exendin-4, or a coagulation factor such as FVIIa and FVIII, or pharmaceutically acceptable salts thereof.

The pharmaceutical compositions of the present invention may be prepared by conventional techniques, e.g. as described in Remington: The Science and Practice of Pharmacy, 19$^{th}$ Ed., 1995. The composition may be in liquid, solid or semisolid form and may further include pharmaceutically acceptable fillers, carriers, diluents or adjuvants, and other inert ingredients and excipients. Furthermore, the pharmaceutical composition can be designed for a slow release of the conjugate.

The compositions can be formulated for any suitable route of administration such as intravenous, intraarterial, intramuscular, subcutaneous, intraperitoneal, subcutaneous, oral, rectal, and transdermal administration, as well as for inhalation. The dosage will depend on the state of the patient, and will be determined as deemed appropriate by the practitioner. The pharmaceutical compositions of the invention may be administered continuously, daily, twice daily, thrice daily or four times daily and/or upon the occurrence of symptoms associated with the condition, for various duration periods, e.g., weeks, months, years, or decades.

The pharmaceutical composition of the invention may be in the form of a sterile injectable aqueous or oleagenous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, without limiting, water, Ringer's solution and isotonic sodium chloride solution.

Pharmaceutical compositions according to the present invention, when formulated for administration route other than parenteral administration, may be in a form suitable for oral use, e.g., as tablets, troches, lozenges, aqueous, or oily suspensions, dispersible powders or granules, emulsions, hard or soft capsules, or syrups or elixirs. Compositions intended for oral use may be prepared according to any method known to the art for the manufacture of pharmaceutical compositions and may further comprise one or more agents selected from sweetening agents, flavoring agents, coloring agents and preserving agents in order to provide pharmaceutically elegant and palatable preparations. Tablets contain the active agent in admixture with non-toxic pharmaceutically acceptable excipients, which are suitable for the manufacture of tablets. These excipients may be, e.g., inert diluents such as calcium carbonate, sodium carbonate, lactose, calcium phosphate, or sodium phosphate; granulating and disintegrating agents, e.g., corn starch or alginic acid; binding agents, e.g., starch, gelatin or acacia; and lubricating agents, e.g., magnesium stearate, stearic acid, or talc. The tablets may be either uncoated or coated utilizing known techniques to delay disintegration and absorption in the gastrointestinal tract and thereby provide a sustained action over a longer period. For example, a time delay material such as glyceryl monostearate or glyceryl distearate may be employed. They may also be coated using the techniques described in the U.S. Pat. Nos. 4,256,108, 4,166, 452 and 4,265,874 to form osmotic therapeutic tablets for control release. The pharmaceutical composition of the invention may also be in the form of oil-in-water emulsion.

The pharmaceutical compositions of the invention may be formulated for controlled release of the conjugate. Such compositions may be formulated as controlled-release matrix, e.g., as controlled-release matrix tablets in which the release of a soluble conjugate is controlled by having the active diffuse through a gel formed after the swelling of a hydrophilic polymer brought into contact with dissolving liquid (in vitro) or gastro-intestinal fluid (in vivo). Many polymers have been described as capable of forming such gel, e.g., derivatives of cellulose, in particular the cellulose ethers such as hydroxypropyl cellulose, hydroxymethyl cellulose, methylcellulose or methyl hydroxypropyl cellulose, and among the different commercial grades of these ethers are those showing fairly high viscosity. In other configurations, the compositions comprise the conjugate formulated for controlled release in microencapsulated dosage form, in which small droplets of the conjugate are surrounded by a coating or a membrane to form particles in the range of a few micrometers to a few millimeters.

The pharmaceutical compositions of the present invention can be used for treatment of various diseases, disorders or conditions, in which administration of the drug Y in the general formula II might be useful.

In particular, in another aspect, the present invention relates to a method for treatment of diabetes mellitus or hyperglycemia in an individual in need thereof, said method comprising administering to said individual an effective amount of a conjugate of formula II, as defined above, wherein the drug Y is insulin, more particularly, a conjugate obtained by nucleophilic substitution of a compound of the general formula Ia-1, preferably compound 1, 2, 3 or 4, with an amino group of insulin.

In still another aspect, the present invention relates to a method for treatment of insulin-dependent diabetes mellitus, non-insulin-dependent diabetes mellitus, or gestational diabetes mellitus, or for prevention of hyperglycemia in an individual in need thereof, said method comprising administering to an individual in need an effective amount of a conjugate of formula II, as defined above, wherein the drug Y is exendin-4, more particularly, a conjugate obtained by nucleophilic substitution of a compound of the general formula Ia-1, preferably compound 1, 2, 3 or 4, with an amino group of exendin-4.

In yet another aspect, the present invention relates to a method for treatment of a patient in need of Factor VIIa or Factor VIII therapy, comprising administering to said patient an effective amount of a conjugate of formula II, as defined above, wherein the drug Y is FVIIa or FVIII, more particularly, a conjugate obtained by nucleophilic substitution of a compound of the general formula Ia-1, preferably compound 1, 2, 3 or 4, with an amino group of FVIIa or FVIII, respectively. In certain embodiments, this method is used for treatment of patients who suffer from hemophilia A.

The invention will now be illustrated by the following non-limiting Examples.

EXAMPLES

Experimental

Materials. Human ($Zn^{2+}$-free) insulin was donated by NovoNordisk (Bagsvalrd, Denmark) or by Biotechnology General (Rehovot, Israel). Insulin-detemir (Levemir®, NovoNordisk) was extensively dialyzed against 0.01 M $NaHCO_3$ and stored at 7° C. until used. The concentration of the insulin-detemir was determined by its absorbance at 279 nm ($\epsilon_{279}$=5800) and/or by acid hydrolyzing an aliquot (in 6 M HCl, for 22 hrs at 110° C.) followed by quantitative amino acid analysis. D-[U-$^{14}$C] glucose (4-7 mCi/mol) was obtained from Du Pont-NEN (Boston, Mass.), type I collagenase (134 U/mg) was purchased from Worthington (Freehold, N.Y.), Exendin-4 (HGEGTFTSDLSKQMEEEAVR-LFIEWLKNGGPSSGAPPPS-$NH_2$; SEQ ID NO: 1) was synthesized by the solid phase method using the multiple peptide synthesizer AMS 422 (Abimed Analysen Technik, GmbH). 11-mercaptoundecanoic acid and 16-mercaptohexadecanoic acid were purchased from Aldrich Ltd (Saint-Louis, Mo.). All other materials used were of analytical grade.

Chemical Synthesis (i) $HO_3S$—$(CH_2)_{15}$—COOH was prepared by performic acid oxidation of 16-mercaptohexadecanoic acid. In particular, 16-mercaptohexadecanoic acid (43.2 mg, 1.5 mmol) was suspended in 14 ml formic acid, hydrogen peroxide (1.0 ml; 5.86 mmoles) was than added, and the reaction was carried out for 14 hrs at 25° C. Formic acid and residual $H_2O_2$ were removed by evaporation, and the product obtained was suspended in $H_2O$ and lyophilized. This procedure was repeated 3 times. The calculated mass of $HO_3S$—$(CH_2)_{15}$—COOH is 336 Da. Found ESMS (M-1)=335.16 Da. The product was obtained in 94% yield.

(ii) $HO_3S$—$(CH_2)_{10}$—COOH was prepared by performic acid oxidation of 11-mercaptoundecanoic acid under the same synthesizing conditions applied for $HO_3S$—$(CH_2)_{10}$—COOH. The calculated mass of $HO_3S$—$(CH_2)_{10}$—COOH is 266 Da. Found ESMS (M-1) 264.96 Da.

(iii) $HO_3S$—$(CH_2)_{15}$—CONHS synthesis. The synthesis was carried out in 1.0 ml DMF containing 34 mg $HO_3S$—$(CH_2)_{15}$—COOH (0.1 mmole) and 38 mg of N-hydroxysuccinimide (0.3 mmole). N-ethyldiisopropylamine (DIPEA) (5.2 µl) was than added to obtain a DIPEA concentration of 30 mM. Solid EDC (40 mg; 0.2 mmoles) were than added. The reaction was carried at 25° C. with stirring over a period of 2 hrs. Hydrochloric acid (3 ml, 0.02M) was than added and the precipitated product was dialyzed overnight against 0.01M HCl at 7° C., to dialyze out DMF, DIPEA, EDC and NHS, which did not participate in the coupling procedure. The product thus obtained was lyophilized. The calculated mass of $HO_3S$—$(CH_2)_{15}$—CONHS is 433 Da. Found ESMS (M-1)=432.18 Da.

(iv) $HO_3S$—$(CH_2)_{10}$—CONHS synthesis. The synthesis was carried out under the same synthesizing conditions applied for $HO_3S$—$(CH_2)_{15}$—CONHS, starting from $HO_3S$—$(CH_2)_{10}$—COOH. The calculated mass is 363 Da. Found ESMS (M-1)=362.05 Da.

(v) Preparation of $PEG_{40}$-$NH_2$. $PEG_{40}$-OSu (m-$PEG_2$-N-hydroxy succinimide ester, Shearwater product) was dissolved at a concentration of 20 mg/ml in 0.1 M $NaHCO_3$, containing 1 M of 1,3 diaminopropane dihydrochloride (Aldrich). The reaction was carried out for 1 h at 25° C. The product was extensively dialyzed against $H_2O$, lyophilized and kept at 7° C. until used.

(vi) Preparation of $PEG_{40}$-$(NH_2)_2$. $PEG_{40}$-OSu (Batch Nof, Sunbright, GL2-400TS) was dissolved at a concentration of 20 mg/ml in an aqueous solution of 0.5 M L-glutamic acid in 1 M $NaHCO_3$ (pH 8.5). Reaction was carried out for 2 hrs at 0° C. The product thus obtained was dialyzed overnight against $H_2O$, lyophilized and dissolved in 0.5 M cystamine-diHCl in $H_2O$ (pH 6.0). Solid EDC was then added (10 mg, 100 molar excess over $PEG_{40}$-$(COOH)_2$) and the reaction was carried out for 2 hrs at 25° C. The product thus obtained was dialyzed extensively against $H_2O$, and lyophilized.

(vii). Preparation of $PEG_{40}$-NHCO—$(CH_2)_{15,10}$—$SO_3^-$ and $PEG_{40}$-[NH—$(CH_2)_{15}$—$SO_3^-]_2$. $PEG_{40}$-$NH_2$ or $PEG_{40}$-$(NH_2)_2$ (10 mg/ml of each in 0.1 M $NaHCO_3$) were treated with 20 molar excess of $^-O_3S$—$(CH_2)_{10}$CONHS or $^-O_3S$—$(CH_2)_{15}$CONHS (presdissolved in 0.1 ml DMF) for 2 hrs a 25° C., and were then dialyzed (24 hrs against 0.01 M HCl and 24 hrs against $H_2O$) and lyophilized. The products thus obtained are TNBS negative, indicating that the amino side chains were fully derivatized.

(viii) Preparation of insulin-CO—$(CH_2)_{15}$—$SO_3H$. To a stirred solution of $Zn^{2+}$-free insulin (29 mg in 4.8 ml 0.1 M Heppes buffer, pH 7.4, 5 µmoles), 6.5 mg $HO_3S$—$(CH_2)_{15}$—CONHS dissolved in 0.2 ml DMF (3 molar excess over insulin) was added. The reaction was carried out for 4 hrs at 0° C., dialyzed extensively against $H_2O$, and lyophilized. The mono-modified derivative of insulin linked to ~∥CO—

$(CH_2)_{15}$—$SO_3^-$ was purified from both unreacted insulin and residual bis-modified derivative using semipreparative HPLC on RP-4 column.

(ix) Preparation of exendin-4-CO—$(CH_2)_{15}$—$SO_3^-$. Exendin-4 (4.2 mg, 1 μmole) was dissolved in 0.1 M Heppes buffer pH 7.4. $^-O_3S$—$(CH_2)_{15}$—CONHS (2.2 mg, 5 μmoles dissolved in 30 μl DMF) was then added and the reaction was carried out for 3 hrs with stirring at 0° C. The product was extensively dialyzed and lyophilized. The mono-modified derivative of exendin-4 linked to ~OC$(CH_2)_{15}$—$SO_3^-$ was purified from both unreacted exendin-4 and residual bis-modified derivative using semi-preperative HPLC on RP-4 column. The mono-modified derivative migrated on analytical HPLC-column as a single symmetric peak with a $R_t$ value of 9.22+0.04 min, whereas native exendin-4 migrates under the same running conditions with a $R_t$ value of 8.2±0.1 min. The calculated mass of exendin-4-CO—$(CH_2)_{15}$—$SO_3H$ is 4505 Da, found by ESMS-analysis, $ES^+$=4504.51±0.89 Da and $ES^-$=4504.44±0.77 Da.

Chemo-Physical Procedures

Ultraviolet spectra were obtained by using a Beckman DU 7500 spectrophotometer in 1-cm path length UV cuvettes. Mass spectra were determined using ESMS technique (Bruker-Reflex-Reflectron model and VG-platform-II electrospray single quadropole mass spectrometer, Micro Mass, respectively).

HPLC analyses were performed using a Spectra-Physics SP8800 liquid chromatography system equipped with an Applied Biosystems 757 variable wavelength absorbance detector and a Spectra-SYSTEM P2000 liquid chromatography system equipped with a Spectra-SYSTEM AS 100 autosampler and a Spectra-SYSTEM UV 1000, all controlled by a ThermoQuest chromatography data system (ThermoQuest Inc., San Jose, Calif.). The column effluents were monitored by UV absorbance at 220 nm.

Analytical reverse phase-HPLC was performed using a pre-packed Chromolith™ Performance RP-18e column (4.6×100 mm, Merck, Darmstadt, Germany). The column was eluted with a binary gradient of 10-100% solution B over 10 min with a flow rate of 3 ml/min (solution A was 0.1% trifluoroacetic acid in $H_2O$ and solution B was 0.1% trifluoroacetic acid in acetonitrile:$H_2O$; 3:1, v/v).

Preparative separations were performed with pre-packed Vydac RP-18 or RP-4 columns (250×22 mm). The column was eluted with 10-100% solution B over 60 min (12 ml/min).

Isothermal scanning calorimetry measurements were performed with ITC200microcalorimeter (Micro Cal LLC Northampton Mass. 01060 USA). Experimental details were carried out according to the ITC200 microcalorimeter users' manual with certain modifications. In particular, the raw data was obtained for 50 injections each of 0.3 μl with intervals of 1 min. The sample cell contained the ligands at a concentration of 20 μM, and the injection syringe contained 400 μM HSA. Both components were dissolved in 0.1 M Hepes buffer pH 7.4. The experiments were conducted at 23° C.

Biological Procedures

Rat adipocytes were prepared from fat pads of male Wistar rats (100-200 g) by collagenase digestion (Rodbell, 1964).

Lipogenesis (during which [U-$^{14}$C] glucose was incorporated into lipids) was carried out as previously described (Moody et al., 1974).

Blood glucose levels were determined at varying time points following administration of insulin, exendin-4, and their derivatives in blood aliquots taken from the tail vein. Glucose analyzer (Beckman Instruments Fullerton, Calif.) was used. Groups consisted of six mice each. Data are presented as means±SE.

Example 1

Synthesizing Sulfonyl-Containing Albumin Binding Probes for the Covalent Attachment to Peptides and Proteins Derivatives resembling long-chain fatty acids but containing a C-terminal sulfonate rather than a carboxylate-anion are not available commercially. We therefore converted 11-mercaptoundecanoic acid (HOOC—$(CH_2)_{10}$—SH) and 16-mercaptohexadecanoic acid. (HOOC—$(CH_2)_{15}$—SH) to the corresponding sulfonated derivatives using performic-acid oxidation as described in Experimental and shown in Scheme 1. Those were subsequently turned into the active esters by linking N-hydroxysuccinimide to their carboxylate moieties. The structures of the intermediates and the final products were validated by mass-spectroscopy. Both compounds $^-O_3S$—$(CH_2)_{10}$—CONHS, 1, and $^-O_3S$—$(CH_2)_{15}$—CONHS, 2, were obtained in >80% overall yields.

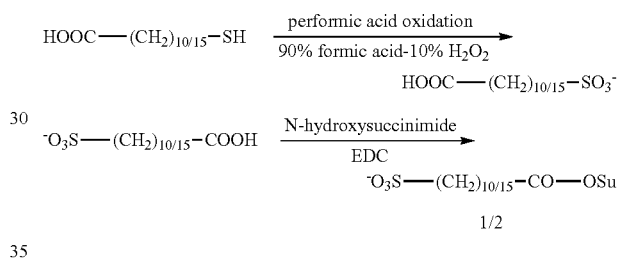

Scheme 1. Synthesis of $^-O_3S$——$(CH_2)_{10/15}$–CO——OSu

Example 2

Figure 1B:
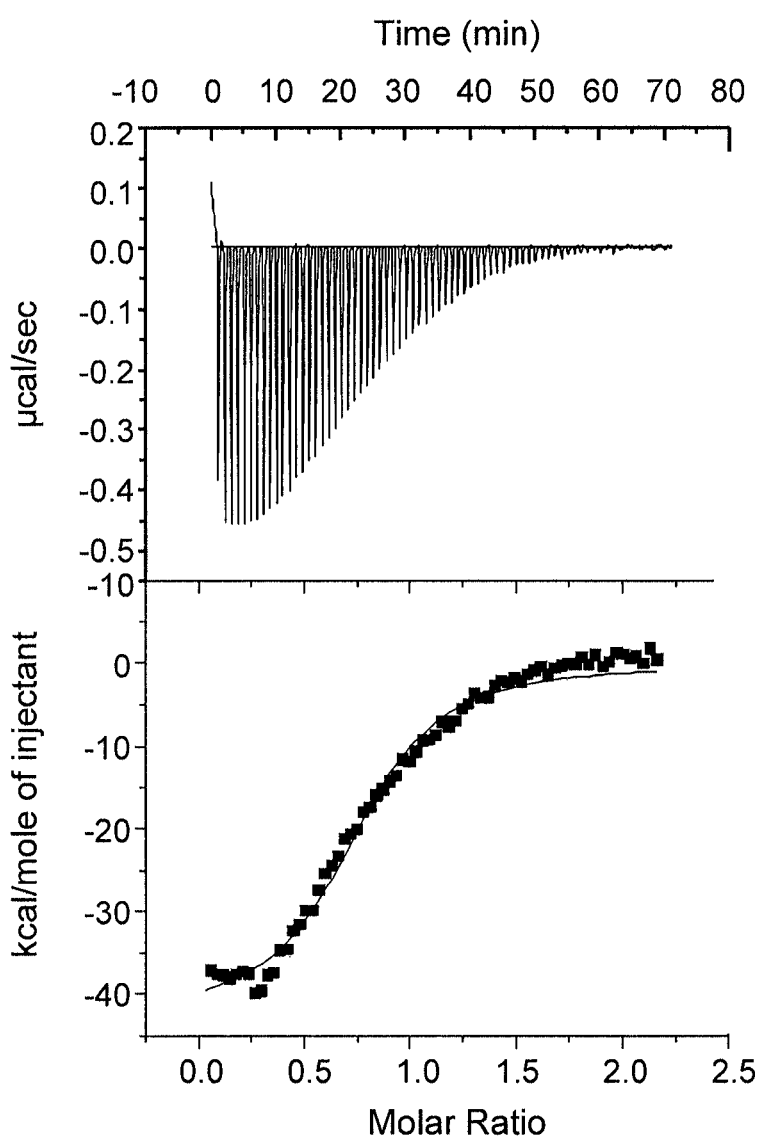
Figure 1C:
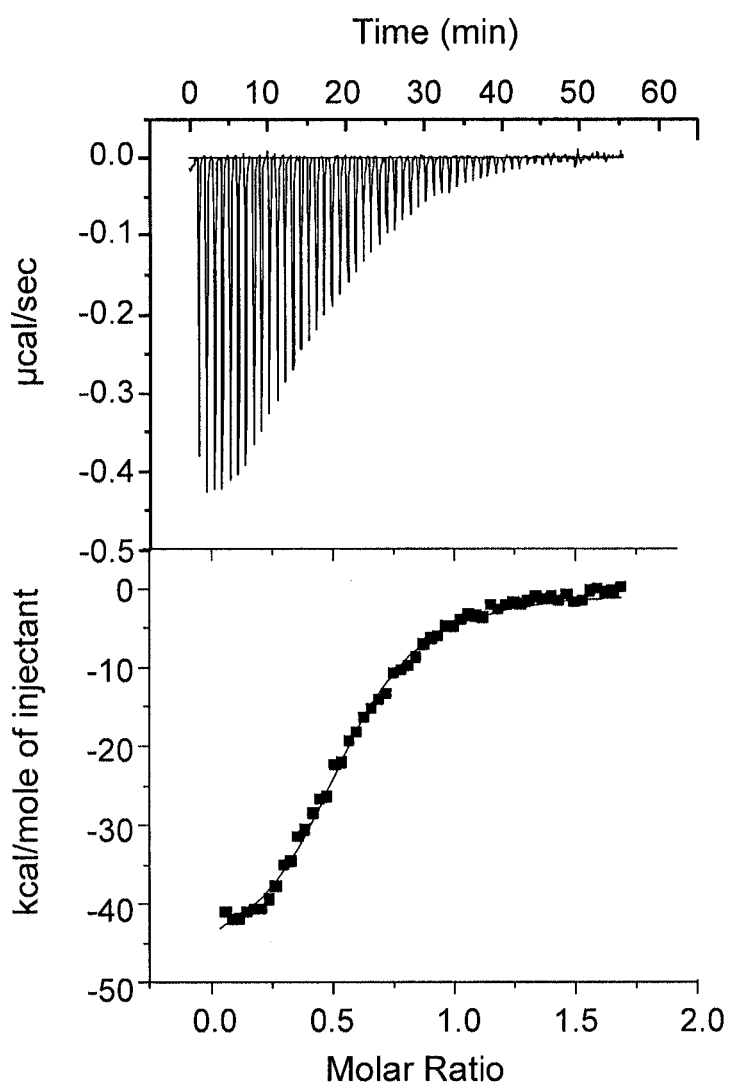

Associating Affinity of Macromolecules Containing ~$(CH_2)_{10}$—$SO_3^-$ and ~$(CH_2)_{15}$—$SO_3^-$ With Human Serum Albumin In this study, the associating affinities of macromolecules containing either a single or pair of covalently-linked ~$(CH_2)_{10/15}$—$SO_3^-$ toward HSA was evaluated using Isothermal Scanning calorimetry (Chaires, 2008) as described in Experimental, wherein PEG chain of 40 kDa (PEG$_{40}$) was used as a model for a macromolecule. As shown in FIG. 1, both PEG$_{40}$-NH—CO—$(CH_2)_{10}$—$SO_3^-$ (1A) and PEG$_{40}$-NH—CO—$(CH_2)_{15}$—$SO_3^-$ (1B) associates with HSA, with Ka values of 0.195±0.0274×$10^6M^{-1}$ and 0.829±0.0821×$10^6M^{-1}$, respectively. PEG$_{40}$ containing a pair of the longer moieties showed a Ka value of 0.83±0.0495×$10^6M^{-1}$ (1C). It is thus concluded that a methylene chain composed of C10 or C15 atoms ending with a C-terminal sulfonate anion, linked to a macromolecule, binds to HSA with Ka values in the range of 0.2-0.8×$10^6 114^{-1}$, wherein no further increase in the affinity is seen when two such moieties are linked to the macromolecule.

Example 3

Chemical and Biological Features of Insulin-CO—$(CH_2)_{15}$—$SO_3H$

The HPLC-purified mono-modified derivative insulin-CO—$(CH_2)_{15}$—$SO_3H$ was prepared as described in Experimental, and the characteristic features of this derivative are summarized in Table 3.

Figure 2:
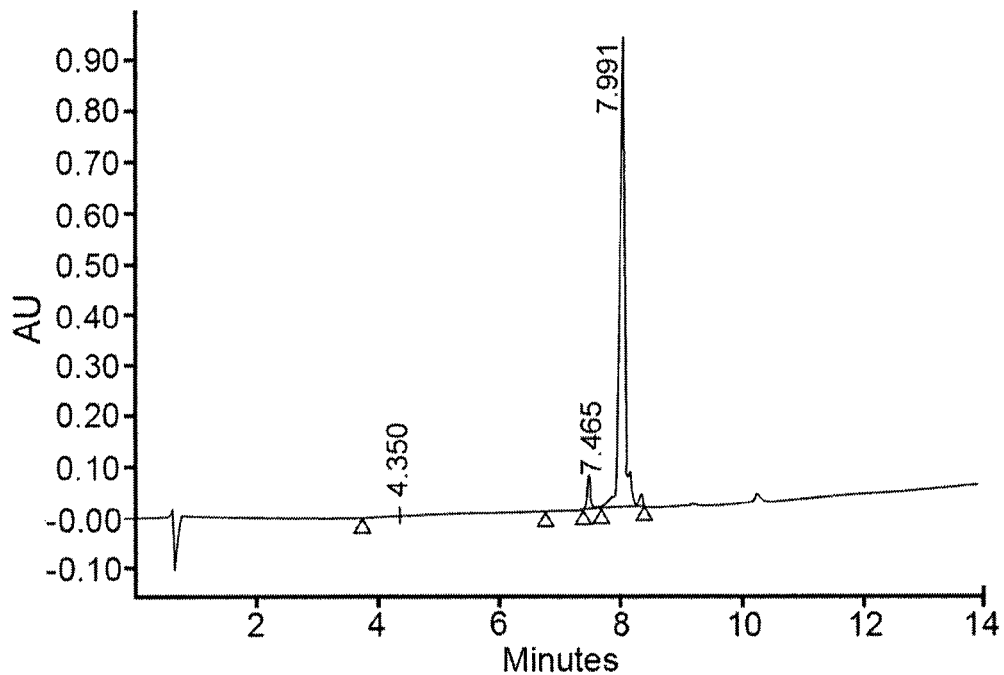
FIG. 2 shows HPLC-analysis of purified insulin-CO—$(CH_2)_{15}$—$SO_3H$. The derivative (30 μg) was loaded onto a chromolite Rp-18e (100×4 mm) column and run with a linear gradient from 0 to 100% solution A (0.1% TFA) to solution B (acetonitrile:$H_2O$ 75:25 in 0.1% TFA) over 10 min, and than in solution B over 4 min at a rate of 3 ml/min. The effluent was monitored at 220 nm.

As particularly shown, insulin-CO—(CH$_2$)$_{15}$—SO$_3$H is soluble in aqueous buffers (pH 7.5-8.0) at a concentration of >10 mg/ml, and has the absorbance of the native hormone ($\epsilon_{279}$=5800). The mono-modified derivative emerged as a symmetric peak on analytical HPLC column with R$_t$=7.991±0.05 minutes (see also FIG. 2). As further found, the mono-modified derivative activates lipogenesis in rat adipocytes at about 20% the efficacy of insulin, yielding a half maximal effect (ED$_{50}$) at a concentration of 0.5±0.03 nM; however, in this specific assay, the biological potency of such albumin-associated insulin derivatives may be significantly reduced due to the presence of BSA (10 mg/ml) as we previously observed with insulin-detemir (ED$_{50}$=2.0±0.2 nM, unpublished data).

TABLE 3

Chemical and biological features of insulin —CO—(CH$_2$)$_{15}$—SO$_3$–

| Characteristic | Ins —CO—(CH$_2$)$_{15}$—SO$_3$– |
|---|---|
| Amino acid composition | Identical to insulin |
| Absorbance at 279 nm$^a$ | $\epsilon_{279}$ = 5800, identical to insulin |
| Analytical HPLC; a single peak, R$_t$ | 7.966 ± 0.025 min$^b$ |
| Mass-spectroscopy (electrospray ionization calculated (m/z)) | 6126 Da$^c$ |
| Found ES– | 6124.98 ± 0.27 Da |
| Found ES+ | 6126.82 ± 0.50 Da |
| Solubility in aqueous buffer (pH 7.5-8.0) | >10 mg/ml |
| Lipogenic potency in rat adipocytes$^d$ | ED$_{50}$ = 0.5 ± 0.03 nM (~20%)$^d$ |

$^a$A derivative with known absorbance at 279 nm was quantitated by hydrolyzing an aliquot in 6 M HCl (110° C., 22 hrs).
$^b$Under the same running conditions, insulin eluted with R$_t$ = 7.30 ± 0.04 min.
$^c$Calculated mass is the molecular weight of human insulin (5807 Da) combined with that of —OC—(CH$_2$)$_{15}$—SO$_3$H (319 Da).
$^d$In this assay, insulin stimulated lipogenesis 4-5 times above basal level, with ED$_{50}$ value of 0.1 ± 0.02 nM (0.58 ng/ml).

Figure 3:
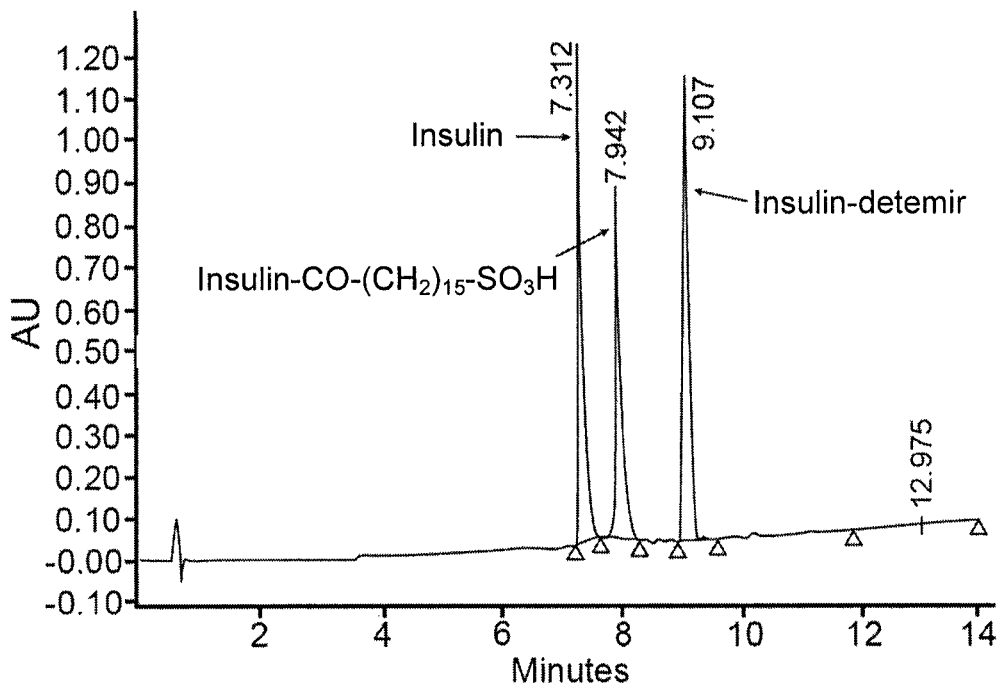
FIG. 3 shows the relative hydrophilicity of insulin-CO—$(CH_2)_{15}$—$SO_3^-$, in comparison to insulin-detemir, as determined by hydrophobic chromatography. A mixture of $Zn^{2+}$-free insulin, HPLC-purified mono-modified insulin-CO—$(CH_2)_{15}$—$SO_3^-$, and insulin-detemir (40 μg each) were loaded onto a chromolite R.P-18e (100×4 mm) column and run under the same running-conditions specified in FIG. 2.

FIG. 3 shows the retention times (R$_t$ values) of insulin, insulin-CO—(CH$_2$)$_{15}$—SO$_3$H, and insulin-detemir loaded on analytical-HPLC-chromolite R.P-18e column. This approach of hydrophobic chromatography yields an estimate of the overall lipophilicity of peptide analogs (Shechter et al., 2010). As shown, insulin, insulin-CO—(CH$_2$)$_{15}$—SO$_3$H and insulin-detemir emerged from the column with R$_t$ values of 7.312, 7.942 and 9.107 min, respectively, indicating that insulin-CO—(CH$_2$)$_{15}$—SO$_3$H is quite hydrophilic in nature, in particular, in comparison to insulin-detemir that contains a single C-14 fatty acid chain covalently linked to lysine B$^{29}$ (Markussen et al., 1996).

Example 4

Glucose Lowering Pattern of Insulin-CO—(CH$_2$)$_{15}$—SO$_3$–

Figure 4:
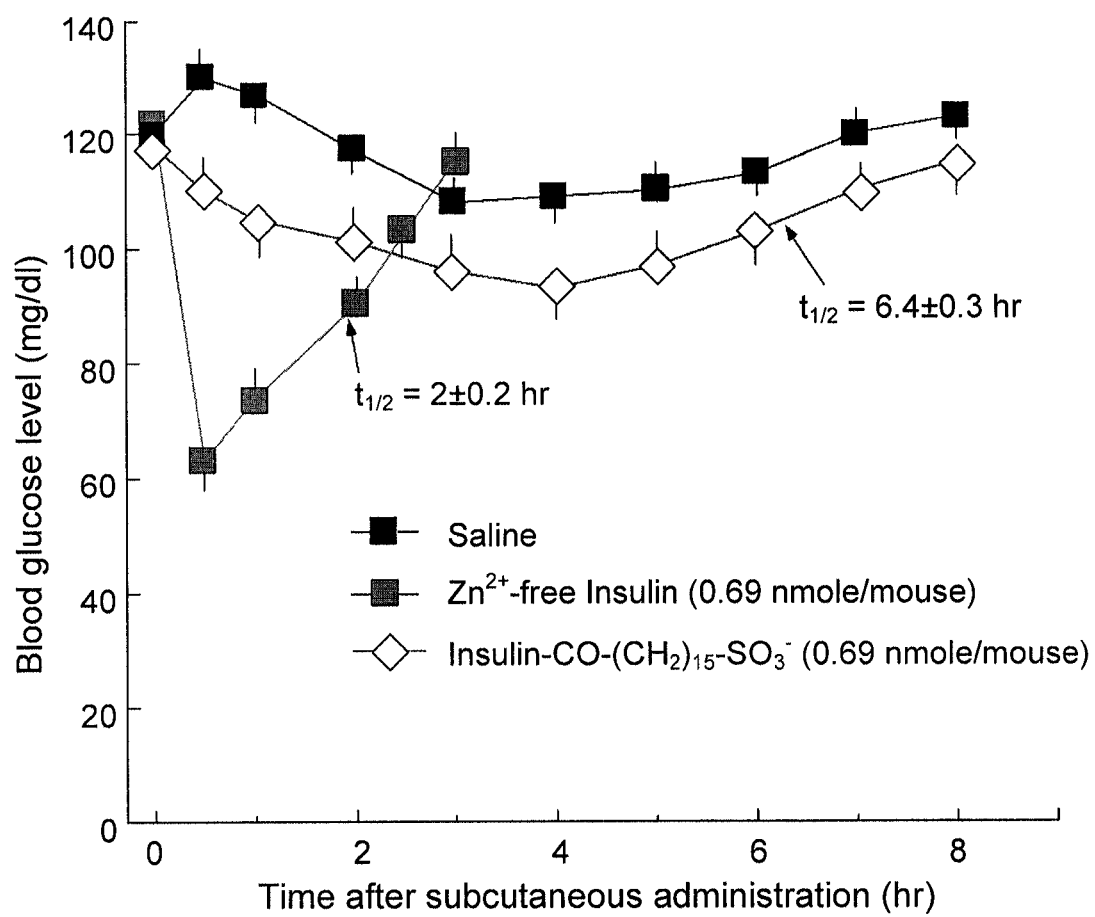
FIG. 4 shows circulating glucose levels in mice following a single subcutaneous administration of insulin-CO—$(CH_2)_{15}$—$SO_3^-$ vs. $Zn^{2+}$-free insulin. CD1-mice were injected subcutaneously with saline (0.2 mi/mouse), $Zn^{2+}$-free insulin (0.69 nmole/mouse in 0.2 ml saline), or insulin-CO—$(CH_2)_{15}$—$SO_3^-$ (0.69 nmole/mouse in 0.2 ml saline), and blood glucose levels were determined at the indicated time points. Each point is the arithmetic mean of n=6 mice±SE.

In this study, we compared the glucose-lowering pattern obtained after a single administration of insulin-CO—(CH$_2$)$_{15}$—SO$_3$H to that of Zn$^{+2}$-free insulin, both administered subcutaneously at a low dose to CD1-mice (0.69 nmole/mouse). As shown in FIG. 4, insulin-CO—(CH$_2$)$_{15}$—SO$_3$H had a flat glucose-lowering pattern (t$_{1/2}$=6.4±0.3 hrs), which was about 3-fold more prolonged than that of insulin (t$_{1/2}$=2±0.2 hrs). In terms of area under the curve, insulin-CO—(CH$_2$)$_{15}$—SO$_3$H resembled that of the native hormone (integrated from FIG. 4), although in terms of lipogenesis in vitro, the former had about 20% the biological potency of insulin as shown in Table 3.

Example 5

Exendin-4-CO—(CH$_2$)$_{15}$—SO$_3$H Facilitates Prolonged Glucose-Lowering Effect in CD1 Mice Following Subcutaneous Administration HPLC-purified exendin-4-CO—(CH$_2$)$_{15}$—SO$_3$H was prepared as described in Experimental, and the glucose-lowering profiles of this derivative and of native exendin-4, subcutaneously administered at a dose of 0.25 nmole/CD1 mice, were then evaluated. As previously observed, the action of this glucagon-like peptide-1 agonist, in this strain of mice, resembles the pharmacodynamic pattern obtained in db/db mice. As further observed, in Type II diabetic patients, circulating blood glucose level, at any dosage of exendin-4 injected, never falls below a threshold level which in CD1 mice amounted to 74±7 mg/dl (Shechter et al., 2003; Tsubery et al., 2004).

Figure 5:
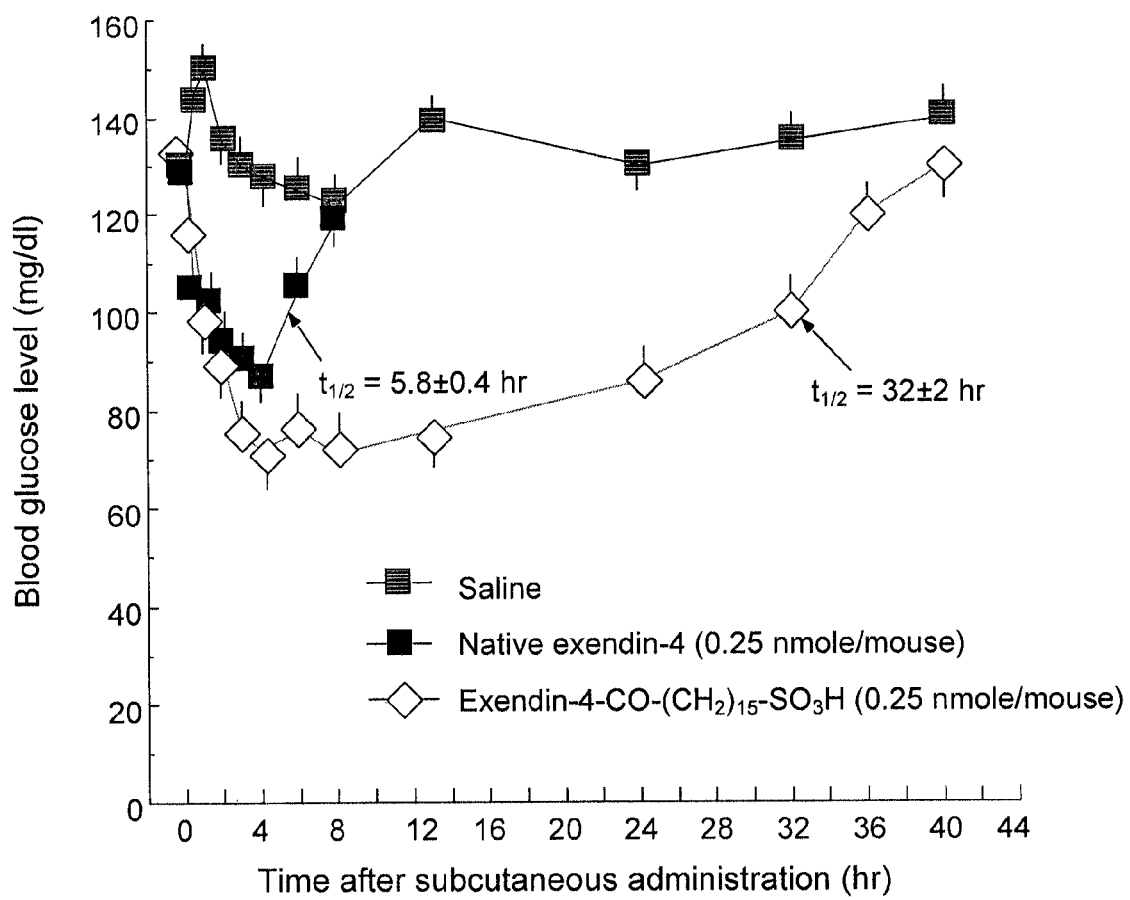
FIG. 5 shows glucose lowering pattern of exendin-4-CO—$(CH_2)_{15}$—$SO_3^-$ following a single subcutaneous administration to CD1-mice. Three groups of CD1-mice (n=6 per group) underwent one subcutaneous administration of saline, native exendin-4 (0.25 nmole/mouse), or exendin-4-CO—$(CH_2)_{15}$—$SO_3^-$ (0.25 nmole/mouse), and circulating glucose levels were monitored at the time points indicated in the figure. Each point is the arithmetic mean of n=6 mice±SE.

As shown in FIG. 5, following subcutaneous administration of Exendin-4-CO—(CH$_2$)$_{15}$—SO$_3$–, glucose level fall to 70±5 mg/dl, and remained at low level over a period of ~24 hrs before slowly returning to the level of the saline-injected CD1 mice. A t$_{1/2}$ value of 32±2 hrs, which is 5.5 times higher than that obtained by the same dose of the native hormone, was obtained. The area under the curve of subcutaneously administered exendin-4-CO—(CH$_2$)$_{15}$—SO$_3$H (as integrated from FIG. 5) exceeded 7±0.1 times that obtained by a similar subcutaneously administered dose of the native hormone.

Figure 6:
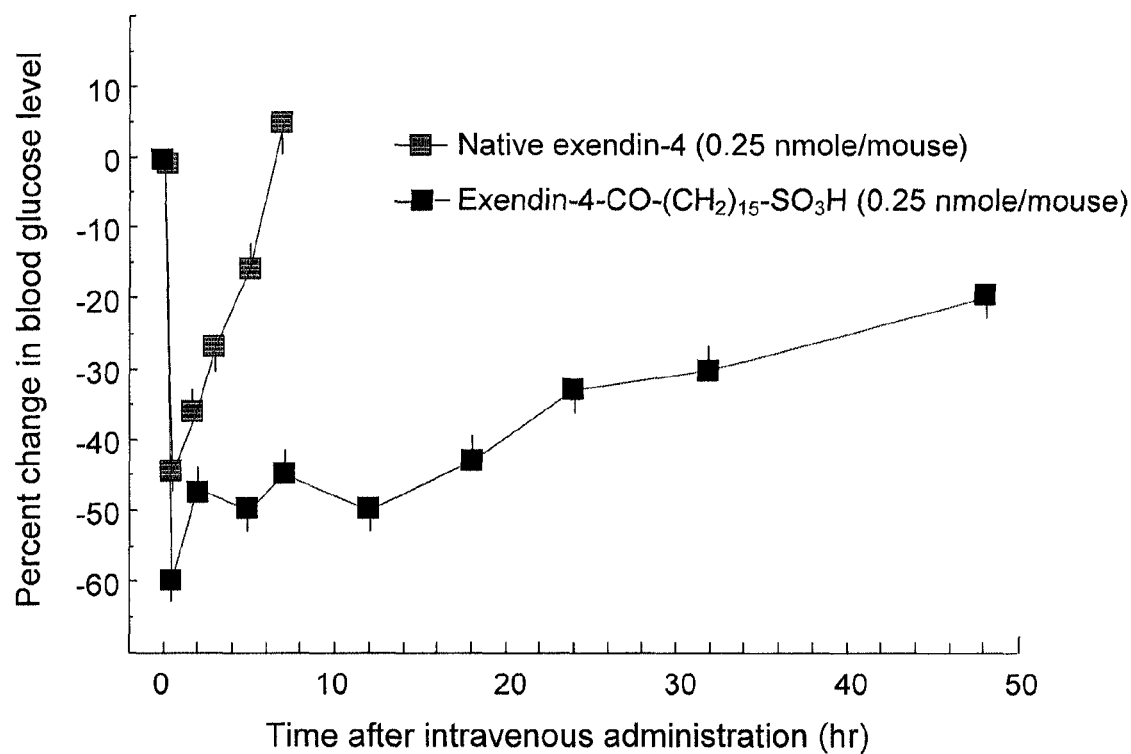
FIG. 6 shows glucose lowering pattern of exendin-4-CO—$(CH_2)_{15}$—$SO_3^-$ following a single intravenous administration to CD1-mice. Three groups of CD1-mice (n=6 per group) underwent one intravenous administration of saline, native exendin-4 (0.25 nmole/mouse), or exendin-4-CO—$(CH_2)_{15}$—$SO_3^-$ (0.25 nmole/mouse), and circulating glucose levels were then monitored. Results are expressed as percent decrease in plasma glucose concentration in the group treated with exendin-4 or exendin-4-CO—$(CH_2)_{15}$—$SO_3^-$, relative to that found in the saline-treated group, measured at the same time point during the day.

In order to evaluate whether the prolonged-acting feature of subcutaneous administered exendin-4-CO—(CH$_2$)$_{15}$—SO$_3$– is, at least in part, due to association with albumin present in the subcutaneous interstitial fluid, causing slower and more prolonged rate of diffusion of this derivative from the subcutis to the circulatory system, exendin-4 and exendin-4-CO—(CH$_2$)$_{15}$—SO$_3$– were administered intravenously. As shown in FIG. 6, intravenously administered exendin-4-CO—(CH$_2$)$_{15}$—SO$_3$– yielded a prolonged glucose-lowering pattern having a t$_{1/2}$ value of 28±2 hrs exceeding that of exendin-4 by 9-10 folds (blood glucose level was still low 48 hrs after administration, which was the last time point measured), indicating that the prolonged-acting feature of exendin-4-CO—(CH$_2$)$_{15}$—SO$_3$– appears to be predominantly the outcome of its association with circulating serum albumin.

Example 6

Designing a Cysteine-Specific Reagent Containing Albumin-Binding Probe for Protracting the Activity of Short-Lived Peptide/Protein Drugs Example 1 describes the synthesis of the sulfonyl-containing albumin binding probes H$_3$OS—(CH$_2$)$_{10/15}$—CONHS, 1/2, and Examples 4 and 5 demonstrate that the covalent-introduction of such probes, in particular 2, to a peptide/protein results in a derivative having high affinity to serum albumin and therefore turns it into a longer-lived species in vivo. It should be noted however that the aforesaid reagents are amino specific having no selectivity toward one or another amino group in a polypeptide chain and as such suffer of some practical deficiencies. For example, addition of –O$_3$S—(CH$_2$)$_{15}$—CONHS to a protein containing several lysine moieties would yield several derivatives of the protein wherein the α-amino group and/or one, two or more of the lysine residues are linked to said reagent, out of which the desirable one would have to be purified, e.g., by HPLC. It is envisioned that engineering a sulthydryl specific reagent containing an albumin binding-probe might overcome this specific "industrial deficiency".

Contrary to the aforesaid, most peptide/protein drugs do not contain a non-bonded cysteine residue, and with the technologies currently available this might confer a practical advantage. A single cysteine moiety can be introduced into a peptide drug during synthesis or into a protein prepared by recombinant technology. Thus, mercapto group specific sulfonyl-containing albumin binding probes, i.e., sulfonyl-containing albumin binding probes capable of specifically reacting with a non-bonded cysteine residue of a peptide/protein, would yield monomodified, well characterized products requiring little or no further purification.

Maleimide is highly specific to sulfhydryls at pH 7.0. Although maleimides react with primary amines at pH>8.0, the reaction rate in these cases is about 1000 times slower than the reaction rate with sulthydryls at pH 7.0. Thus, adding stoichiometric amount of a MAL-containing reagent to a non-bonded cysteine containing peptide/protein would yield homogenous solely cysteine-modified product.

In this experiment, the MAL-containing albumin binding probes $HO_3S$—$(CH_2)_{10/15}$—CO—NH—$(CH_2)_3$-maleimido, 6/10 respectively, are prepared by coupling the active ester $HO_3S$—$(CH_2)_{10/15}$—CONHS, 1/2, with $H_2N$—$(CH_2)_3$-MAL in DMF (4 hrs; 25° C.) containing N-ethyldiisopropylamine (30 mM), as shown in Scheme 2. In particular, a ratio of 1:2 $HO_3S$—$(CH_2)_{10/15}$—CONHS to $H_2N$—$(CH_2)_3$-MAL is applied, and the reaction mixture is then dialyzed at pH 3.0 (where the MAL-function is fully stable) and lyophilized. The dialysis removes both the DMF and the organic base, and should further remove excess $H_2N$—$(CH_2)_3$-MAL, leaving the desired product only inside the dialysis tube. In case $H_2N$—$(CH_2)_3$-MAL is not dialyzed out, it can be removed by HPLC-purification.

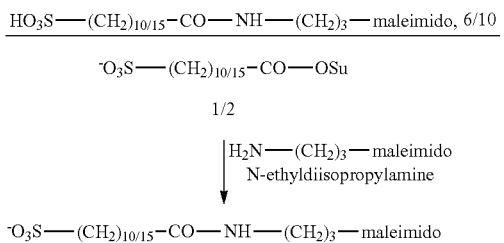

Scheme 2. Synthesis of
$HO_3S$—$(CH_2)_{10/15}$–CO—NH—$(CH_2)_3$—maleimido, 6/10

REFERENCES

Carter D. C., Ho J. X., Structure of serum albumin, *Adv Protein Chem*, 1994, 45, 153-203

Chae S. Y., Choi Y. G., Son S., Jung S. Y., Lee D. S., Lee K. C., The fatty acid conjugated exendin-4 analogs for type 2 antidiabetic therapeutics, *J Control Release*, 2010, 144(1), 10-16

Chaires J. B., calorimetry and thermodynamics in drug design, *Annu Rev Biophys*, 2008, 37, 135-151

Goodman L., Gilman A., *The Pharmacological Basis of Therapeutic*, 1995, Mc Graw-Hill, New-York Jonassen I., Havelund S., Ribel U., Plum A., Loftager M., Hoeg-Jensen T., Volund A., Markussen J., Biochemical and physiological properties of a novel series of long-acting insulin analogs obtained by acylation with cholic acid derivatives, *Pharm Res*, 2006, 23(1), 49-55

Kurtzhals P., Havelund S., Jonassen I., Kiehr B., Larsen U. D., Ribel U., Markussen J., Albumin binding of insulins acylated with fatty acids: characterization of the ligand-protein interaction and correlation between binding affinity and timing of the insulin effect in vivo, *Biochem J*, 1995, 312, 725-731

Kurtzhals P., Haveland S., Jonassen I., Kiehr B., Ribel U., Markussen J., Albumin binding and time action of acylated insulins in various species. *J. Pharmaceut. Sci.*, 1996, 85, 304-308

Kurtzhals P., Haveland S., Jonassen I. B., Markussen J., Effect of fatty acids and selected drugs on the albumin binding of a long-acting, acylated insulin analogue, *J. Pharmaceut. Sci.*, 1997, 86, 1365-1368

Markussen J., Havelund S., Kurtzhals P., Andersen A. S., Halstrom. J., Hasselager E., Larsen U. D., Ribel U., Schaffer L., Vad K., Jonassen I., Soluble, fatty acid acylated insulins bind to albumin and show protracted action in pigs, *Diabetologia*, 1996, 39(3), 281-288

Moody A. J., Stan M. A., Stan M., Gliemann J., A simple free fat cell bioassay for insulin, *Horm Metab Res*, 1974, 6(1), 12-16

Peters T. J., The albumin molecule: its structure and chemical properties, All about albumin, Biochemistry, Genetics and medical applications., in *Academic Press, Inc.*, 1996, San Diego, Calif. p. 24-54

Poulsen H. L., Subcutaneous interstitial fluid albumin concentration in long-term diabetes mellitus, *Scand. J. Clin. Lab. Invest.*, 1973, 32, 167-173

Richieri G. V., And A., Kleinfeld A. M., Interactions of long-chain fatty acids and albumin: determination of free fatty acid levels using the fluorescent probe ADIFAB, *Biochemistry*, 1993, 32(29), 7574-7580

Roda A., Cappelleri G., Aldini R., Roda E., Barbara L., Quantitative aspects of the interaction of bile acids with human serum albumin, *J Lipid Res*, 1982, 23(3), 490-495

Rodbell M., Metabolism of isolated fat cells. I. Effects of hormones on glucose metabolism and lipolysis, *J Biol Chem*, 1964, 239, 375-380

Rolin B., Larsen M. O., Gotfredsen C. F., Deacon C. F., Carr R. D., Wilken M., Knudsen. L. B., The long-acting GLP-1 derivative NN2211 ameliorates glycemia and increases beta-cell mass in diabetic mice, *Am J Physiol Endocrinol Metab*, 2002, 283(4), E745-52

Sasson K., Marcus Y., Lev-Goldman V., Rubinraut S., Fridkin M., Shechter Y., Engineering prolonged-acting prodrugs employing an albumin-binding probe that undergoes slow hydrolysis at physiological conditions, *J Control Release*, 2010, 142(2), 214-220

Shechter Y., Tsubery H., Fridkin M., [2-Sulfo-9-fluorenylmethoxy carbonyl]$_3$-exendin-4—a long-acting glucose-lowering prodrug, *Biochem Biophys Res Commun*, 2003, 305(2), 386-391

Shechter Y., Heldman E., Sasson K., Bachar T., Popova M., Fridkin M., Delivery of neuropeptide from the periphery to the brain: studies with enkephalin, *ACS Chemical Neuroscience*, 2010, 1(5), 399-406

Son S., Chae S. Y., Kim C. W., Choi Y. G., Jung S. Y., Lee S., Lee K. C., Preparation and structural, biochemical, and pharmaceutical characterizations of bile acid-modified long-acting exendin-4 derivatives, *J Med Chem*, 2009, 52(21), 6889-6896

Tsubery H., Mironchik M., Fridkin M., Shechter Y., Prolonging the action of protein and peptide drugs by a novel approach of reversible polyethylene glycol modification, *J Biol Chem*, 2004, 279(37), 38118-24

---

The invention claimed is:

1. A compound of the general formula I:

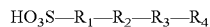

$$HO_3S\!-\!R_1\!-\!R_2\!-\!R_3\!-\!R_4 \qquad I$$

wherein:
$R_1$ is selected from the group consisting of ($C_9$-$C_{25}$) alkylene, ($C_9$-$C_{25}$)alkenylene, and ($C_9$-$C_{25}$) alkynylene, optionally substituted by one or more groups each independently selected from the group consisting of halogen, —$COR_5$, —$COOR_5$, —$OCOOR_5$, —$OCON(R_5)_2$, —$NO_2$, —$SR_5$, —$OR_5$, —$N(R_5)_2$, —$CON(R_5)_2$, —$SO_2R_5$, —$SO_3H$, —S(=O)$R_5$, ($C_6$-$C_{10}$)aryl, ($C_1$-$C_4$)alkylene-($C_6$-$C_{10}$)aryl, heteroaryl, and ($C_1$-$C_4$)alkylene-heteroaryl, wherein said ($C_9$-$C_{25}$) alkylene is optionally further interrupted by one or more groups each independently selected from the group consisting of —S—, —NH—CO—, —CO—NH—, —N($C_6$-$C_{10}$aryl)-, ($C_6$-$C_{10}$)arylene-diyl, and heteroarylenediyl, and said ($C_9$-$C_{25}$)alkenylene and ($C_9$-$C_{25}$)alkynylene is optionally further interrupted by one or more groups each independently selected from the group consisting of —S—, —O—, —N—, —NH—CO—, —CO—NH—, —N($C_1$-$C_8$alkyl)-, —N($C_6$-$C_{10}$aryl)-, ($C_6$-$C_{10}$)arylene-diyl, and heteroarylenediyl;
$R_2$ is —CO— or —S—;
$R_3$ is absent or selected from the group consisting of —NH—$R_6$-maleimido, and -maleimido-$R_6$-maleimido;
$R_4$ is absent or a leaving group;
$R_5$ each independently is H or ($C_1$-$C_8$)alkyl; and
$R_6$ is selected from the group consisting of ($C_1$-$C_{12}$) alkylene, ($C_2$-$C_{12}$)alkenylene, and ($C_2$-$C_{12}$)alkynylene, optionally substituted by one or more groups each independently selected from the group consisting of halogen, —$COR_5$, —$COOR_5$, —$OCOOR_5$, —$OCON(R_5)_2$, —CN, —$NO_2$, —$SR_5$, —$OR_5$, —$N(R_5)_2$, —$CON(R_5)_2$, —$SO_2R_5$, and —S(=O)$R_5$, and further optionally interrupted by one or more identical or different heteroatoms selected from the group consisting of S, O and N, and/or at least one group each independently selected from the group consisting of —NH—CO—, —CO—NH—, —N($C_1$-$C_8$alkyl)-, and —N($C_6$-$C_{10}$aryl)-,
provided that (i) when $R_2$ is —CO—, $R_3$ is absent and $R_4$ is a leaving group, or $R_3$ is —NH—$R_6$-maleimido and $R_4$ is absent; and (ii) when $R_2$ is —S—, $R_3$ is absent and $R_4$ is a leaving group, or $R_3$ is -maleimido-$R_6$-maleimido and $R_4$ is absent.

2. The compound of claim 1, wherein the leaving group is selected from the group consisting of —O—($CH_2$)$_2$—CN, —Cl, N-hydroxysuccinimide (—OSu), 2-nitrophenoxy, 4-nitrophenoxy, 2,3,4,5,6-pentachloro phenoxy, isoindoline-1,3-dione-2-oxy, benzenesulfanyl, nitrobenzenesulfanyl, pyridine-2-sulfanyl, pyridine-3-sulfanyl, and pyridine-4-sulfanyl.

3. The compound of claim 1, wherein $R_1$ is ($C_9$-$C_{25}$) alkylene, optionally substituted by one or more groups each independently selected from the group consisting of halogen, —COH, —COOH, —OCOOH, —$OCONH_2$, —CN, —$NO_2$, —SH, —OH, —$NH_2$, —$CONH_2$, —$SO_2H$, —$SO_3H$, —S(=O)H, ($C_1$-$C_2$)alkylene-($C_6$-$C_{10}$)aryl, and ($C_1$-$C_2$)alkylene-heteroaryl, and further optionally interrupted by one or more groups each independently selected from the group consisting of —S—, —NH—CO—, and —CO—NH—.

4. The compound of claim 3, wherein $R_1$ is ($C_{10}$-$C_{20}$) alkylene, optionally substituted by one or more groups each independently is —$CH_2$—($C_6$-$C_{10}$)aryl, and further interrupted by at least one group each independently is —NH—CO—, or —CO—NH—.

5. The compound of claim 3, wherein said ($C_6$-$C_{10}$)aryl is phenyl, hydroxyphenyl, carboxyphenyl, nitrophenyl, cianophenyl, mercaptophenyl, aminocarbonylphenyl, fluorophenyl, chlorophenyl, or bromophenyl; and said heteroaryl is 2-indolyl, 3-indolyl, 4-indolyl, 5-indolyl, 6-indolyl, 7-indolyl, 2-imidazolyl, 4-imidazolyl, or 5-imidazolyl.

6. The compound of claim 4, wherein $R_1$ is —($CH_2$)$_{10}$—, —($CH_2$)$_{15}$—, —($CH_2$)$_{10}$—CO—NH—CH($CH_2$-phenyl)-, or —($CH_2$)$_{15}$—CO—NH—CH($CH_2$-phenyl)-.

7. The compound of claim 1, wherein:
(i) $R_2$ is —CO—; $R_3$ is absent; and $R_4$ is —O—($CH_2$)$_2$—CN, —Cl, N-hydroxysuccinimide (—OSu), 2-nitrophenoxy, 4-nitrophenoxy, 2,3,4,5,6-pentachlorophenoxy, isoindoline-1,3-dione-2-oxy, benzenesulfanyl, nitrobenzenesulfanyl, pyridine-2-sulfanyl, pyridine-3-sulfanyl, or pyridine-4-sulfanyl;
(ii) $R_2$ is —CO—; $R_3$ is —NH—$R_6$-maleimido; and $R_4$ is absent;
(iii) $R_2$ is —S—; $R_3$ is absent; and $R_4$ is benzenesulfanyl, nitrobenzenesulfanyl, pyridine-2-sulfanyl, pyridine-3-sulfanyl, or pyridine-4-sulfanyl, preferably pyridine-2-sulfanyl, or pyridine-4-sulfanyl; or (iv) R$_2$ is —S—; R$_3$ is -maleimido-R$_6$-maleimido; and R$_4$ is absent.

8. The compound of claim 7, wherein R$_6$ is (C$_1$-C$_{12}$) alkylene, optionally substituted by one or more groups each independently selected from the group consisting of halogen, —COH, —COOH, —OCOOH, —OCONH$_2$, —CN, —NO$_2$, —SH, —OH, —NH$_2$, —CONH$_2$, —SO$_2$H, and —S(=O)H, and further optionally interrupted by one or more identical or different heteroatoms selected from the group consisting of S, O and N, and/or at least one group each independently is —NH—CO—, or —CO—NH—.

9. The compound of claim 8, wherein R$_6$ is (C$_1$-C$_{10}$) alkylene, optionally interrupted by one or more groups each independently is —NH—CO—, or —CO—NH—.

10. The compound of claim 9, wherein R$_6$ is —CH$_2$—, —(CH$_2$)$_3$—, —(CH$_2$)$_3$—NH—CO—(CH$_2$)$_3$—, or —(CH$_2$)$_2$—NH—CO—(CH$_2$)$_5$—.

11. The compound of claim 7, wherein (i) R$_1$ is —(CH$_2$)$_{10}$—, —(CH$_2$)$_{15}$—, —(CH$_2$)$_{10}$—CO—NH—CH(CH$_2$-phenyl)-, or —(CH$_2$)$_{15}$—CO—NH—CH(CH$_2$-phenyl)-; R$_2$ is —CO—; R$_3$ is absent; and R$_4$ is —Osu; (ii) R$_1$ is —(CH$_2$)$_{10}$—, or —(CH$_2$)$_{15}$—; R$_2$ is —CO—; R$_3$ is —NH—R$_6$-maleimido; R$_4$ is absent; and R$_6$ is —CH$_2$—, —(CH$_2$)$_3$—, —(CH$_2$)$_3$—NH—CO—(CH$_2$)$_3$—, or —(CH$_2$)$_2$—NH—CO—(CH$_2$)$_5$—; or (iii) R$_1$ is —(CH$_2$)$_{15}$—; R$_2$ is —S—; R$_3$ is absent; and R$_4$ is pyridine-2-sulfanyl, or pyridine-4-sulfanyl.

12. A conjugate of the general formula II:

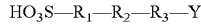

HO$_3$S—R$_1$—R$_2$—R$_3$—Y  II

Y is a moiety of a drug containing at least one amino or mercapto group, linked through said at least one amino or mercapto group;

R$_1$ is selected from the group consisting of (C$_9$-C$_{25}$) alkylene, (C$_9$-C$_{25}$)alkenylene, and (C$_9$-C$_{25}$) alkynylene, optionally substituted by one or more groups each independently selected from the group consisting of halogen, —COR$_5$, —COOR$_5$, —OCOOR$_5$, —OCON(R$_5$)$_2$, —CN, —NO$_2$, —SR$_5$, —OR$_5$, —N(R$_5$)$_2$, —CON(R$_5$)$_2$, —SO$_2$R$_5$, —SO$_3$H, —S(=O)R$_5$, (C$_6$-C$_{10}$)aryl, (C$_1$-C$_4$)alkylene-(C$_6$-C$_{10}$)aryl, heteroaryl, and (C$_1$-C$_4$)alkylene-heteroaryl, wherein said (C$_9$-C$_{25}$)alkylene is optionally further interrupted by one or more groups each independently selected from the group consisting of —S—, —NH—CO—, —CO—NH—, —N(C$_6$-C$_{10}$aryl)-, (C$_6$-C$_{10}$)arylene-diyl, and heteroarylenediyl, and said (C$_9$-C$_{25}$)alkenylene and (C$_9$-C$_{25}$)alkynylene is optionally further interrupted by one or more groups each independently selected from the group consisting of —S—, —O—, —N—, —NH—CO—, —CO—NH—, —N(C$_1$-C$_8$alkyl)-, —N(C$_6$-C$_{10}$aryl)-, (C$_6$-C$_{10}$)arylene-diyl, and heteroarylenediyl;

R$_2$ is —CO— or —S—;

R$_3$ is absent or selected from the group consisting of —NH—R$_6$-maleimido, and -maleimido-R$_6$-maleimido;

R$_5$ each independently is H or (C$_1$-C$_8$)alkyl; and

R$_6$ is selected from the group consisting of (C$_1$-C$_{12}$) alkylene, (C$_2$-C$_{12}$)alkenylene, and (C$_2$-C$_{12}$)alkynylene, optionally substituted by one or more groups each independently selected from the group consisting of halogen, —COR$_5$, —COOR$_5$, —OCOOR$_5$, —OCON(R$_5$)$_2$, —CN, —NO$_2$, —SR$_5$, —OR$_5$, —N(R$_5$)$_2$, —CON(R$_5$)$_2$, —SO$_2$R$_5$, and —S(=O)R$_5$, and further optionally interrupted by one or more identical or different heteroatoms selected from the group consisting of S, O and N, and/or at least one group each independently selected from the group consisting of —NH—CO—, —CO—NH—, —N(C$_1$-C$_8$alkyl)-, and —N(C$_6$-C$_{10}$aryl)-, provided that when R$_2$ is —CO— and R$_3$ is absent, Y is linked through said at least one amino group, and when R$_2$ is —S— or R$_3$ is present, Y is linked through said at least one mercapto group.

13. The conjugate of claim 12, wherein R$_1$ is (C$_9$-C$_{25}$) alkylene, optionally substituted by one or more groups each independently selected from the group consisting of halogen, —COH, —COOH, —OCOOH, —OCONH$_2$, —CN, —NO$_2$, —SH, —OH, —NH$_2$, —CONH$_2$, —SO$_2$H, —SO$_3$H, or —S(=O)H, (C$_1$-C$_2$)alkylene-(C$_6$-C$_{10}$)aryl, and (C$_1$-C$_2$)alkylene-heteroaryl, and further optionally interrupted by one or more groups each independently selected from the group consisting of —S—, —NH—CO—, and —CO—NH—.

14. The conjugate of claim 13, wherein R$_1$ is (C$_{10}$-C$_{20}$) alkylene, optionally substituted by one or more groups each independently is —CH$_2$—(C$_6$-C$_{10}$)aryl, and further interrupted by at least one group each independently is —NH—CO—, or —CO—NH—.

15. The conjugate of claim 13, wherein said (C$_6$-C$_{10}$)aryl is phenyl, hydroxyphenyl, carboxyphenyl, nitrophenyl, cianophenyl, mercaptophenyl, aminocarbonylphenyl, fluorophenyl, chlorophenyl, or bromophenyl; and said heteroaryl is 2-indolyl, 3-indolyl, 4-indolyl, 5-indolyl, 6-indolyl, 7-indolyl, 2-imidazolyl, 4-imidazolyl, or 5-imidazolyl.

16. The conjugate of claim 14, wherein R$_1$ is —(CH$_2$)$_{10}$—, —(CH$_2$)$_{15}$—, —(CH$_2$)$_{10}$—CO—NH—CH(CH$_2$-phenyl)-, or —(CH$_2$)$_{15}$—CO—NH—CH(CH$_2$-phenyl)-.

17. The conjugate of claim 12, wherein:
(i) R$_2$ is —CO—; and R$_3$ is absent;
(ii) R$_2$ is —CO—; and R$_3$ is —NH—R$_6$-maleimido;
(iii) R$_2$ is —S—; and R$_3$ is absent; or
(iv) R$_2$ is —S—; and R$_3$ is -maleimido-R$_6$-maleimido.

18. The conjugate of claim 17, wherein R$_6$ is (C$_1$-C$_{12}$) alkylene, optionally substituted by one or more groups each independently selected from the group consisting of halogen, —COH, —COOH, —OCOOH, —OCONH$_2$, —CN, —NO$_2$, —SH, —OH, —NH$_2$, —CONH$_2$, —SO$_2$H, and —S(=O)H, and further optionally interrupted by one or more identical or different heteroatoms selected from the group consisting of S, O and N, and/or at least one group each independently is —NH—CO—, or —CO—NH—.

19. The conjugate of claim 18, wherein R$_6$ is (C$_1$-C$_{10}$) alkylene, optionally interrupted by one or more groups each independently is —NH—CO—, or —CO—NH—.

20. The conjugate of claim 19, wherein R$_6$ is —CH$_2$—, —(CH$_2$)$_3$—, —(CH$_2$)$_3$—NH—CO—(CH$_2$)$_3$—, or —(CH$_2$)$_2$—NH—CO—(CH$_2$)$_5$—.

21. The conjugate of claim 17, wherein (i) R$_1$ is —(CH$_2$)$_{10}$—, —(CH$_2$)$_{15}$—, —(CH$_2$)$_{10}$—CO—NH—CH(CH$_2$-phenyl)-, or —(CH$_2$)$_{15}$—CO—NH—CH(CH$_2$-phenyl)-; R$_2$ is —CO—; and R$_3$ is absent; (ii) R$_1$ is —(CH$_2$)$_{10}$—, or —(CH$_2$)$_{15}$—; R$_2$ is —CO—; R$_3$ is —NH—R$_6$-maleimido; and R$_6$ is —CH$_2$—, —(CH$_2$)$_3$—, —(CH$_2$)$_3$—NH—CO—(CH$_2$)$_3$—, or —(CH$_2$)$_2$—NH—CO—(CH$_2$)$_5$—; or (iii) R$_1$ is —(CH$_2$)$_{15}$—; R$_2$ is —S—; and R$_3$ is absent.

22. The conjugate of claim 12, wherein Y is a peptide or a protein drug of low or medium molecular weight such as insulin, an interferon such as IFN-α2, a PYY agonist such as the peptide PYY$_{3-36}$, an exendin such as exendin-3 or exendin-4, an exendin analog or exendin agonist, atrial natriuretic peptide (ANP), human growth hormone (hGH), erythropoietin, TNF-α, calcitonin, gonadotropin releasing hormone (GnRH), a GnRH analog, hirudin, glucagon, a coagulation factor such as Factor VIIa and Factor VIII, or a monoclonal antibody fragment such as anti-TNF-α monoclonal antibody fragment; or a small molecule such as an antimicrobial drug or an anticancer drug.

23. The conjugate of claim 22, wherein $R_1$ is —$(CH_2)_{10}$—, or —$(CH_2)_{15}$—, —$(CH_2)_{10}$—CO—NH—CH($CH_2$-phenyl)-, or —$(CH_2)_{15}$—CO—NH—CH($CH_2$-phenyl)-; $R_2$ is —CO—; $R_3$ is absent; and Y is insulin, exendin-4, Factor VIIa, or Factor VIII.

24. A pharmaceutical composition comprising a conjugate according to claim 12, or a pharmaceutically acceptable salt thereof, and a pharmaceutically acceptable carrier.

25. A method for treatment of diabetes mellitus or hyperglycemia in an individual in need thereof, comprising administering to said individual an effective amount of a conjugate according to claim 17 wherein $R_2$ is —CO—, $R_3$ is absent, and Y is insulin.

26. A method for treatment of insulin-dependent diabetes mellitus, non-insulin-dependent diabetes mellitus, or gestational diabetes mellitus, or for prevention of hyperglycemia in an individual in need thereof, comprising administering to said individual an effective amount of a conjugate according to claim 17 wherein $R_2$ is —CO—, $R_3$ is absent, and Y is exendin-4.

27. A method for treatment of a patient in need of Factor VIIa or Factor VIII therapy, comprising administering to said patient an effective amount of a conjugate according to claim 17 wherein $R_2$ is —CO—, $R_3$ is absent, and Y is Factor VIIa or Factor VIII, respectively.

\* \* \* \* \*